United States Patent
Pimentel et al.

(10) Patent No.: US 10,690,679 B2
(45) Date of Patent: *Jun. 23, 2020

(54) METHODS AND SYSTEMS FOR DISTINGUISHING IRRITABLE BOWEL SYNDROME FROM INFLAMMATORY BOWEL DISEASE AND CELIAC DISEASE

(71) Applicant: Cedars-Sinai Medical Center, Los Angeles, CA (US)

(72) Inventors: Mark Pimentel, Los Angeles, CA (US); Christopher Chang, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/152,806

(22) Filed: Oct. 5, 2018

(65) Prior Publication Data

US 2019/0187153 A1 Jun. 20, 2019

Related U.S. Application Data

(63) Continuation of application No. 14/878,416, filed on Oct. 8, 2015, now Pat. No. 10,132,814.

(60) Provisional application No. 62/085,825, filed on Dec. 1, 2014, provisional application No. 62/061,877, filed on Oct. 9, 2014.

(51) Int. Cl.
*G01N 33/68* (2006.01)

(52) U.S. Cl.
CPC ... *G01N 33/6854* (2013.01); *G01N 2333/205* (2013.01); *G01N 2800/065* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,691,151 A | 11/1997 | Braun et al. |
| 6,805,852 B2 | 10/2004 | Lin et al. |
| 6,861,053 B1 | 3/2005 | Lin et al. |
| 7,048,906 B2 | 5/2006 | Lin et al. |
| 7,056,686 B2 | 6/2006 | Lin et al. |
| 7,081,239 B2 | 7/2006 | Lin |
| 7,244,412 B2 | 7/2007 | Lin |
| 7,452,857 B2 | 11/2008 | Lin et al. |
| 7,585,838 B2 | 9/2009 | Lin et al. |
| 7,605,240 B2 | 10/2009 | Lin et al. |
| 7,608,245 B2 | 10/2009 | Lin |
| 7,615,207 B2 | 11/2009 | Lin |
| 7,718,608 B2 | 5/2010 | Lin et al. |
| 7,736,622 B2 | 6/2010 | Lin et al. |
| 7,935,799 B2 | 5/2011 | Lin et al. |
| 8,110,177 B2 | 2/2012 | Lin et al. |
| 8,197,805 B2 | 6/2012 | Lin et al. |
| 8,388,935 B2 | 3/2013 | Lin et al. |
| 8,562,952 B2 | 10/2013 | Lin et al. |
| 9,110,081 B2 | 8/2015 | Pimentel et al. |
| 9,358,276 B2 | 6/2016 | Lin et al. |
| 9,851,361 B2 | 12/2017 | Pimentel |
| 9,869,676 B2 | 1/2018 | Pimentel et al. |
| 10,132,814 B2 | 11/2018 | Pimentel et al. |
| 10,151,752 B2 | 12/2018 | Pimentel et al. |
| 2003/0170726 A1 | 9/2003 | Fradelizi et al. |
| 2004/0018528 A1 | 1/2004 | Morimoto et al. |
| 2006/0127359 A1 | 6/2006 | Borrelli |
| 2006/0193871 A1 | 8/2006 | Lin |
| 2007/0212691 A1 | 9/2007 | Yamasaki et al. |
| 2009/0298060 A1 | 12/2009 | Lal et al. |
| 2011/0183337 A1 | 7/2011 | Von Stein et al. |
| 2011/0294726 A1 | 12/2011 | Pimentel et al. |
| 2011/0305704 A1 | 12/2011 | Pimentel et al. |
| 2012/0088257 A1 | 4/2012 | Mouthon et al. |
| 2013/0331283 A1 | 12/2013 | McAndrew et al. |
| 2014/0206636 A1 | 7/2014 | Lin et al. |
| 2015/0023394 A1 | 8/2015 | Pimentel et al. |
| 2016/0103136 A1 | 4/2016 | Pimentel |
| 2017/0095543 A1 | 4/2017 | Lin et al. |
| 2018/0196063 A1 | 7/2018 | Pimentel et al. |
| 2018/0231551 A1 | 8/2018 | Pimentel et al. |
| 2018/0364255 A1 | 12/2018 | Pimentel et al. |

FOREIGN PATENT DOCUMENTS

| | | |
|---|---|---|
| AU | 2002256254 B2 | 5/2007 |
| AU | 2007201246 A1 | 3/2009 |
| AU | 2010213708 B2 | 12/2015 |
| AU | 2014331841 A2 | 3/2016 |
| AU | 2015330872 A1 | 4/2017 |
| AU | 2016201529 | 6/2018 |

(Continued)

OTHER PUBLICATIONS

PCT/US2013/005626 International Search Report and Written Opinion dated Aug. 18, 2014; 14 pages.

(Continued)

*Primary Examiner* — Elly-Gerald Stoica

(74) *Attorney, Agent, or Firm* — Linda B. Huber; Nixon Peabody LLP

(57) ABSTRACT

Described herein are methods and systems for distinguishing irritable bowel syndrome (IBS) from inflammatory bowel disease (IBD) and celiac disease. The methods and systems can utilize the detection of anti-vinculin antibodies and anti-CdtB antibodies to distinguish IBS from IBD and celiac disease. Further described are methods for selecting a therapy to treat IBS, IBD or celiac disease.

7 Claims, 6 Drawing Sheets

Specification includes a Sequence Listing.

(56) References Cited

FOREIGN PATENT DOCUMENTS

| | | |
|---|---|---|
| BR | PI1008058-9 A8 | 3/2016 |
| BR | 112016007474-2 A2 | 9/2017 |
| CA | 2923651 A1 | 4/2015 |
| CA | 2962493 A1 | 4/2016 |
| CA | 2444548 C | 6/2016 |
| CL | 1943-2011 | 2/2012 |
| CL | 2011-1944 | 2/2012 |
| CL | 2016000820 A1 | 9/2016 |
| CN | 105744956 A1 | 7/2016 |
| CN | 107003308 A | 8/2017 |
| CO | 16091069 | 9/2016 |
| DE | 602013027637.4 | 10/2017 |
| EP | 1 385 476 | 2/2004 |
| EP | 2 261 665 B1 | 6/2004 |
| EP | 1 200 828 B1 | 10/2007 |
| EP | 2 261 664 A2 | 12/2010 |
| EP | 2 305 213 A2 | 4/2011 |
| EP | 1 811 303 B1 | 6/2011 |
| EP | 2 256 498 B1 | 4/2015 |
| EP | 2 895 856 | 7/2015 |
| EP | 2 267 445 B1 | 8/2016 |
| EP | 3054977 A1 | 8/2016 |
| EP | 3204771 A1 | 8/2017 |
| EP | 2396652 B | 12/2017 |
| EP | 3349004 | 7/2018 |
| IN | 201727012044 A | 6/2017 |
| JP | 2009-102401 | 5/2009 |
| JP | 4653936 | 12/2010 |
| JP | 2017502253 A | 1/2017 |
| JP | 2017531801 A | 10/2017 |
| KR | 20160062161 A | 6/2016 |
| KR | 20170067795 A | 6/2017 |
| MX | 2015-048142 | 7/2015 |
| MX | 2016004167 A | 6/2016 |
| MX | 348670 | 6/2017 |
| MX | 2017055077 | 7/2017 |
| MX | 2017-045632 | 11/2017 |
| PE | 08822016 A1 | 9/2016 |
| RU | 2397178 C1 | 8/2010 |
| SG | 11201702395W A | 4/2017 |
| SG | 11201601733V A | 5/2018 |
| WO | WO 01/11077 A2 | 2/2001 |
| WO | WO 01/11334 A2 | 2/2001 |
| WO | WO 2002/083926 A2 | 10/2002 |
| WO | WO 2004/024097 A2 | 3/2004 |
| WO | 2005029091 A2 | 3/2005 |
| WO | WO 2010/093801 A1 | 8/2010 |
| WO | WO 2012/007913 A2 | 1/2012 |
| WO | WO 2014/042828 A2 | 3/2014 |
| WO | WO 2015/054529 A1 | 4/2015 |
| WO | WO 2016/057772 A1 | 4/2016 |
| WO | 2018140869 A1 | 8/2018 |

OTHER PUBLICATIONS

PCT/US2013/005626 International Preliminary Report on Patentability dated Aug. 18, 2014; 12 pages.
PCT/US2010/023911 International Search Report and Written Opinion dated May 14, 2010; 11 pages.
PCT/US2010/023911 International Preliminary Report on Patentability dated Aug. 16, 2011; 8 pages.
PCT/US2014/059957 International Search Report and Written Opinion dated Jan. 8, 2015; 11 pages.
PCT/US2014/059957 International Preliminary Report on Patentability dated Apr. 21, 2016; 9 pages.
PCT/US2015/054655 International Search Report and Written Opinion dated Feb. 12, 2016; 7 pages.
International Search Report and Written Opinion of PCT/US2018/015723, dated Apr. 24, 2018, 13 pages.
Extended European Search Report of EP 15849701.6 dated Feb. 8, 2018, 10 pages.
EP Application No. 17206465.1 Extended Search Report dated Apr. 20, 2018; 13 pages.
EP Application No. 10741728.9 Extended Search Report dated Oct. 17, 2014; 7 pages.
EP Application No. 13837424.4 Extended Search Report dated May 9, 2016; 8 pages.
Singapore Application No. 11201601733V Written Opinion dated Apr. 17, 2017; 8 pages.
Written Opinion of Singapore Application No. 11201702395W, dated Nov. 24, 2017, 8 pages.
Abuoun et al. Cytolethal Distending Toxin (CDT)-Negative Campylobacter jejuni Strains and Anti-CDT Neutralizing Antibodies are Induced during Human Infection but Not during Colonization in Chickens. Infection and Immunity (2005). 73(5): 3053-3062.
Air et al. Mechanism of Antigenic Variation in an Individual Epitope on Influenza Virus N9 Neuraminidase. Journal of Virology (1990). 64(12):5797-5803.
Bourke, B. Campylobacter infection: small bowel and colon. Current Opinion in Gastroenterology. (2002). 18:4-9.
Bradesi et al., Novel Therapeutic Approaches in IBS, Current Opinion in Pharmacology, 2007, vol. 7(6), pp. 598-604.
Cambridge et al. Anti-neutrophil antibodies in inflammatory bowel disease: prevalence and diagnostic role. Gut (2013). 33:668-674.
Carey et al. A prospective evaluation of the pathogenesis of detrusor instability in woman, using electron microscopy and immunohistochemistry. BJU International (2000). 86:970-976.
Colman, PM. Effects of amino acid sequence changes on antibody-antigen interactions. Res Immunol (1994). 145(1):33-6.
Dib et al., Targets of Anti-Endothelial Cell Antibodies in Pulmonary Hypertension and Scleroderma, 2012, Eur. Respir. J., vol. 39, pp. 1405-1414.
Dunlop et al. Relative Importance of Enterochromaffin Cell Hyperplasia, Anxiety, and Depression in Postinfectious IBS. Gastroenterology (2003). 125:1651-1659.
EP Application No. 14851688.3 Extended Search Report dated Mar. 10, 2017; 10 pages.
Fox et al. Gastroenteritis in NF-kappaB-deficient mice is produced with wildtype Campylobacter jejuni but not with C. jejuni lacking cytolethal distending toxin despite persistent colonization with both strains. Infection & Immunity (2004). 72(2):1116-25.
Hickey et al. Campylobacter jejuni Cytolethal Distending Toxin Mediates Release of Interleukin-8 from Intestinal Epithelial Cells. Infection and Immunity (2000). 68(12):6535-6541.
Lembo et al. Use of serum biomarkers in a diagnostic test for irritable bowel syndrome. Alimentary Pharmacology & Therapeutics (2009). 29:834-842.
Mariuzza et al. The structural basis of antigen-antibody recognition. Annu Rev Biophys Biophys Chem (1987). 16:139-59. Abstract Only.
Morales et al. Antibodies to Cytolethal Distending Toxin of Campylobacter Jejuni Bind to Enteric Neuronal Elements: Further Evidence for Molecular Mimicry. Gastroenterology (2012). 142(5): Suppl 1.
Morales et al. Effect of Rifaximin Treatment on Anti-Vinculin Antibodies in Ibs with Diarrhea. Gastroenterology (2016).150(4). Supplement 1. p. S-695.
Morales et al. Tu2056 Antibodies to Cytolethal Distending Toxin B and Auto-Antibodies to Human Vinculin are Elevated in Ibs Subjects. Gastroenterology (2013). 144(5): Suppl. 1, p. S-914.
Moss-Morris et al. To "Lump" or to "Split" the Functional Somatic Syndromes: Can Infections and Emotional Risk Factors Differentiate between the Onset of Chronic Fatigue Syndrome and Irritable Bowel Syndrome. Psychosomatic Medicine (2006). 68:463-469.
Neal et al. Prevalence of Gastrointestinal Symptoms Six Months after Bacterial Gastroenteritis and Risk Factors for Development of the Irritable Bowel Syndrome: Postal Survey of Patients. BMJ (1997). 314:779, 14 pages.
Nelson et al. Vinculin Activators Target Integrins from within the Cell to Increase Melanoma Sensitivity to Chemotherapy. Molecular Cancer Research (2011). 9(6):1-12.
Nemeth et al. Altered Cytoskeleton in Smooth Muscle of Aganglionic Bowel. Arch Pathol Lab Med (2002). 126:692-696.
Novak, K. A Serologic Test for Irritable Bowel Syndrome and Other News from ACG. Gastroenterology Press Highlights (2013); pp.

(56) References Cited

OTHER PUBLICATIONS 1-2. Retrieved from: <www.gastrojournal.org/pb/assets/raw/Health%20Advance/journals/ygast/November26_PressHighlight3.pdf5 on Feb. 3, 2016.

Peng et al. a-Catenin Uses a Novel Mechanism to Activate Vinculin. The Journal of Biological Chemistry (2012). 287(10): 7728-7737.

Pimentel et al. A New Rat Model Links Two Complementary Theories in Irritable Bowel Syndrome. Digestive Diseases and Sciences (2007). 53(4):982-989.

Pimentel et al. Anti-vinculin antibodies: Multicenter validation of a diagnostic blood test for irritable bowel syndrome. The American Journal of Gastroenterology (2013). 108:1887; p. S571. Abstract Only.

Pimentel et al. Autoimmunity to vinculin in humans may be important in the pathophysiology of IBS. Gastroenterology (2014). 146(5); suppl 1, Su2020. Abstract Only.

Pimentel et al. Development and Validation of a Biomarker for Diarrhea-Predominant Irritable Bowel Syndrxome in Human Subjects. PLoS One (2015). 10(5): pp. 1-12.

Purdy et a. Characterisation of cytolethal distending toxin (CDT) mutants of Campylobacter jejuni. J. Med. Microbiol. (2000). 49: pp. 473-479.

Regent et al., Identification of Target Antigens of Anti-Endothelial Cell and Anti-Vascular Smooth Muscle Cell Antigodies in Patients with Giant Cell Arteritis: a Proteomic Approach, 2011, Arthritis Research & Therapy, 13: R107, 15 Pages.

Rezaie et al. Assessment of Anti-Vinculin and Anti-CdtB Antibodies in IBS Subtypes. Gastroenterology (2016).150(4). Supplement 1. p. S62.

Rezaie et al. Assessment of Anti-Vinculin and Anti-Cytolethal Distending Toxin B Antibodies in Subtypes of Irritable Bowel Syndrome, 2017, Digestive Diseases and Sciences, vol. 62(6), pp. 1480-1485.

Rolle et al. Structural basis of voiding dysfunction in megacystis microcolon intestinal hypoperistalsis syndrome. Journal of Pediatric Urology (2006). 2:277-284.

Spiller et al. Increased rectal mucosal enteroendocrine cells, T lymphocytes, and increased gut permeability following acute Campylobacter enteritis and inpost-dysenteric irritable bowel syndrome. Gut (2000). 47:804-811.

Suh et al. Patients with irritable bowel syndrome or constipation have an increased risk for ischaemic colitis. Alimentary Pharmacology & Therapeutics (2007). 25:681-692.

Sung et al. Antibody to Cytolethal Distending Toxin of Campylobacter Jejuni Stains Small Bowel Myenteric Neuromuscular Elements in Control and C. Jejuni Exposed Rats: A Possible Role of Molecular Mimicry. Gastroenterology (2010). 138(5). p. S-770.

Trees et al. Genome Sequences of 228 Shiga Toxin-Producing *Escherichia coli* Isolates and 12 Isolates Representing Other Diarrheagenic *E. coli* Pathotypes. Genome Announc (2014). 2(4): 3 pages.

Triantafyllou et al. Evaluating the Role of Cytolethal Distending Toxin in the Development of Small Intestinal Bacterial Overgrowth in a Rat Model Post-Infectious IBS. Gastroenterology (2014). 146(5): suppl 1, Su1424. Abstract Only.

Turkay et al. Noninvasive Methods in Evaluation of Inflammatory Bowel Disease: Where Do We Stand Now? An Update. Clinics (2010). 65(2):221-31.

Jee et al., ICC Density Predicts Bacterial Overgrowth in a Rat Model of Post-Infectious IBS, 2010, World J. Gastroenterol, vol. 16(29), pp. 3680-3686.

Weller et al., Complete Sequence of Human Vinculin and Assignment of the Gene to Chromosome 10, 1990, Proceedings of the National Academy of Sciences of the USA, vol. 87, pp. 5667-5671.

SEQUENCE LISTING

<160> NUMBER OF SEQ ID NOS: 7

<210> SEQ ID NO 1
<211> LENGTH: 267
<212> TYPE: PRT
<213> ORGANISM: Campylobacter coli

<400> SEQUENCE: 1

```
Met Lys Lys Ile Val Phe Leu Ile Leu Ser Phe Asn Val Leu Phe Ala
1               5                   10                  15

Ala Leu Glu Asn Tyr Asn Thr Gly Thr Trp Asn Leu Gln Gly Ser Ser
            20                  25                  30

Ala Ala Thr Glu Ser Lys Trp Asn Val Ser Ile Arg Gln Leu Ile Thr
        35                  40                  45

Gly Ala Asn Pro Met Asp Val Leu Ala Val Gln Glu Ala Gly Val Leu
    50                  55                  60

Pro Ser Thr Ala Met Met Thr Pro Arg Gln Val Gln Pro Val Gly Val
65                  70                  75                  80

Gly Ile Pro Ile His Glu Tyr Ile Trp Asn Leu Gly Ser Val Ser Arg
                85                  90                  95

Pro Ser Ser Val Tyr Ile Tyr Tyr Ser Arg Val Asp Val Gly Ala Asn
            100                 105                 110

Arg Val Asn Leu Ala Ile Val Ser Arg Val Gln Ala Asp Glu Val Phe
        115                 120                 125

Val Leu Pro Pro Thr Val Ala Ser Arg Pro Ile Ile Gly Ile Arg
    130                 135                 140

Ile Gly Asn Asp Ala Phe Phe Asn Ile His Ala Leu Ala Ser Gly Gly
145                 150                 155                 160

Asn Asp Ala Gly Ala Ile Val Ala Ala Val Asp Met Phe Phe Arg Asn
                165                 170                 175

Arg Pro Asp Ile Asn Trp Met Ile Leu Gly Asp Phe Asn Arg Glu Ser
            180                 185                 190

Gly Ala Leu Val Thr Leu Leu Asp Pro Asp Leu Arg Ala Arg Thr Arg
        195                 200                 205

Val Val Val Pro Pro Ser Ser Thr Gln Thr Ser Gly Arg Thr Ile Asp
    210                 215                 220
```

Tyr Ala Ile Thr Gly Asn Ser Asn Thr Ala Ala Leu Tyr Asn Pro Pro
225                 230                 235                 240

Pro Ile Val Ala Ile Leu Ala Leu Glu Gly Leu Arg Thr Phe Leu Ala
                245                 250                 255

Ser Asp His Phe Pro Val Asn Phe Arg Arg Pro
            260                 265

<210> SEQ ID NO 2
<211> LENGTH: 804
<212> TYPE: DNA
<213> ORGANISM: Campylobacter coli

<400> SEQUENCE: 2
atgaaaaaaa tagtattttt gattttaagt tttaatgtat tatttgccgc tttagaaaat      60
tacaacaccg gaacttggaa tttgcaaggc tcatcagctg caactgaaag caaatggaat     120
gttagtataa acaactcat aaccggtgca atcctatgg atgttttagc tgttcaagaa     180
gcggggtttt tacctagtac agctatgatg actcctagac aggtacaacc cgtgggcgtg     240
ggtattccta tacatgaata catatggaat ttaggctctg tatcaagacc tagctctgtt     300
tatatatatt attctagagt ggatgtagga gcaaatcgtg tgaatttagc tatcgttagc     360
agagtgcaag cggatgaagt ttttgtttta cccctccaa cagttgcttc aagacctatt     420
ataggcatac gcataggcaa tgatgctttt ttcaatatac acgctctagc aagtggggga     480
aatgacgcag gagccattgt cgctgctgtg gatatgtttt ttagaaatag acctgatatt     540
aattggatga tttaggcga ttttaataga gaatcaggcg ccttagtaac cttgctagat     600
cctgacttaa gagcacgcac tcgcgtagtt gttccgcctt cttctacgca aacaagtgga     660
agaacgattg attatgctat cactggaaat tccaacactg cagctttata caacccacca     720
ccgatagttg cgattttagc tttagaagga ttaagaacct ttttggcttc agatcatttt     780
cctgtaaatt ttagaagacc ttag                                            804

<210> SEQ ID NO 3
<211> LENGTH: 17
<212> TYPE: PRT
<213> ORGANISM: Campylobacter jejuni

<400> SEQUENCE: 3

Leu Asp Tyr Ala Ile Thr Gly Asn Ser Asn Arg Gln Gln Thr Tyr Thr
1               5                   10                  15

Pro

<210> SEQ ID NO 4
<211> LENGTH: 18
<212> TYPE: PRT
<213> ORGANISM: Campylobacter jejuni

<400> SEQUENCE: 4

Cys Leu Asp Tyr Ala Ile Thr Gly Asn Ser Asn Arg Gln Gln Thr Tyr
1               5                   10                  15

Thr Pro

<210> SEQ ID NO 5
<211> LENGTH: 265
<212> TYPE: PRT
<213> ORGANISM: Campylobacter jejuni

<400> SEQUENCE: 5

```
Met Lys Lys Ile Ile Cys Leu Phe Leu Ser Phe Asn Leu Ala Phe Ala
1               5                   10                  15

Asn Leu Glu Asn Phe Asn Val Gly Thr Trp Asn Leu Gln Gly Ser Ser
            20                  25                  30

Ala Ala Thr Glu Ser Lys Trp Ser Val Ser Val Arg Gln Leu Val Ser
                35                  40                  45

Gly Ala Asn Pro Leu Asp Ile Leu Met Ile Gln Glu Ala Gly Thr Leu
50                  55                  60

Pro Arg Thr Ala Thr Pro Thr Gly Arg His Val Gln Gln Gly Gly Thr
65                  70                  75                  80

Pro Ile Asp Glu Tyr Glu Trp Asn Leu Gly Thr Leu Ser Arg Pro Asp
                85                  90                  95

Arg Val Phe Ile Tyr Tyr Ser Arg Val Asp Val Gly Ala Asn Arg Val
                100                 105                 110

Asn Leu Ala Ile Val Ser Arg Met Gln Ala Glu Glu Val Ile Val Leu
            115                 120                 125

Pro Pro Pro Thr Thr Val Ser Arg Pro Ile Ile Gly Ile Arg Asn Gly
130                 135                 140

Asn Asp Ala Phe Phe Asn Ile His Ala Leu Ala Asn Gly Gly Thr Asp
145                 150                 155                 160

Val Gly Ala Ile Ile Thr Ala Val Asp Ala His Phe Ala Asn Met Pro
                165                 170                 175

Gln Val Asn Trp Met Ile Ala Gly Asp Phe Asn Arg Asp Pro Ser Thr
                180                 185                 190

Ile Thr Ser Thr Val Asp Arg Glu Leu Ala Asn Arg Ile Arg Val Val
            195                 200                 205

Phe Pro Thr Ser Ala Thr Gln Ala Ser Gly Gly Thr Leu Asp Tyr Ala
210                 215                 220

Ile Thr Gly Asn Ser Asn Arg Gln Gln Thr Tyr Thr Pro Leu Leu
225                 230                 235                 240

Ala Ala Ile Leu Met Leu Ala Ser Leu Arg Ser His Ile Val Ser Asp
                245                 250                 255

His Phe Pro Val Asn Phe Arg Lys Phe
                260                 265

<210> SEQ ID NO 6
<211> LENGTH: 51
<212> TYPE: DNA
<213> ORGANISM: Campylobacter jejuni

<400> SEQUENCE: 6
cttgattatg caattacagg aaattcaaat agacaacaaa cctatactcc a          51

<210> SEQ ID NO 7
<211> LENGTH: 1066
<212> TYPE: PRT
<213> ORGANISM: Homo sapiens

<400> SEQUENCE: 7

Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
            35                  40                  45
```

```
Ala Ala Val Ser Asn Leu Val Arg Val Gly Lys Glu Thr Val Gln Thr
            50                  55                  60
Thr Glu Asp Gln Ile Leu Lys Arg Asp Met Pro Pro Ala Phe Ile Lys
 65                  70                  75                  80
Val Glu Asn Ala Cys Thr Lys Leu Val Gln Ala Gln Met Leu Gln
                 85                  90                  95
Ser Asp Pro Tyr Ser Val Pro Ala Arg Asp Tyr Leu Ile Asp Gly Ser
                100                 105                 110
Arg Gly Ile Leu Ser Gly Thr Ser Asp Leu Leu Thr Phe Asp Glu
            115                 120                 125
Ala Glu Val Arg Lys Ile Ile Arg Val Cys Lys Gly Ile Leu Glu Tyr
            130                 135                 140
Leu Thr Val Ala Glu Val Val Glu Thr Met Glu Asp Leu Val Thr Tyr
145                 150                 155                 160
Thr Lys Asn Leu Gly Pro Gly Met Thr Lys Met Ala Lys Met Ile Asp
                165                 170                 175
Glu Arg Gln Gln Glu Leu Thr His Gln Glu His Arg Val Met Leu Val
            180                 185                 190
Asn Ser Met Asn Thr Val Lys Glu Leu Leu Pro Val Leu Ile Ser Ala
        195                 200                 205
Met Lys Ile Phe Val Thr Thr Lys Asn Ser Lys Asn Gln Gly Ile Glu
210                 215                 220
Glu Ala Leu Lys Asn Arg Asn Phe Thr Val Glu Lys Met Ser Ala Glu
225                 230                 235                 240
Ile Asn Glu Ile Ile Arg Val Leu Gln Leu Thr Ser Trp Asp Glu Asp
                245                 250                 255
Ala Trp Ala Ser Lys Asp Thr Glu Ala Met Lys Arg Ala Leu Ala Ser
            260                 265                 270
Ile Asp Ser Lys Leu Asn Gln Ala Lys Gly Trp Leu Arg Asp Pro Ser
        275                 280                 285
Ala Ser Pro Gly Asp Ala Gly Glu Gln Ala Ile Arg Gln Ile Leu Asp
        290                 295                 300
Glu Ala Gly Lys Val Gly Glu Leu Cys Ala Gly Lys Glu Arg Arg Glu
305                 310                 315                 320
Ile Leu Gly Thr Cys Lys Met Leu Gly Gln Met Thr Asp Gln Val Ala
                325                 330                 335
Asp Leu Arg Ala Arg Gly Gln Gly Ser Ser Pro Val Ala Met Gln Lys
            340                 345                 350
Ala Gln Gln Val Ser Gln Gly Leu Asp Val Leu Thr Ala Lys Val Glu
            355                 360                 365
Asn Ala Ala Arg Lys Leu Glu Ala Met Thr Asn Ser Lys Gln Ser Ile
        370                 375                 380
Ala Lys Lys Ile Asp Ala Ala Gln Asn Trp Leu Ala Asp Pro Asn Gly
385                 390                 395                 400
Gly Pro Glu Gly Glu Gln Ile Arg Gly Ala Leu Ala Glu Ala Arg
                405                 410                 415
Lys Ile Ala Glu Leu Cys Asp Asp Pro Lys Glu Arg Asp Asp Ile Leu
            420                 425                 430
Arg Ser Leu Gly Glu Ile Ser Ala Leu Thr Ser Lys Leu Ala Asp Leu
        435                 440                 445
Arg Arg Gln Gly Lys Gly Asp Ser Pro Glu Ala Arg Ala Leu Ala Lys
450                 455                 460
Gln Val Ala Thr Ala Leu Gln Asn Leu Gln Thr Lys Thr Asn Arg Ala
```

-continued

```
          465                 470                 475                 480
Val Ala Asn Ser Arg Pro Ala Lys Ala Ala Val His Leu Glu Gly Lys
                    485                 490                 495
Ile Glu Gln Ala Gln Arg Trp Ile Asp Asn Pro Thr Val Asp Asp Arg
                    500                 505                 510
Gly Val Gly Gln Ala Ala Ile Arg Gly Leu Val Ala Glu Gly His Arg
                    515                 520                 525
Leu Ala Asn Val Met Met Gly Pro Tyr Arg Gln Asp Leu Leu Ala Lys
                    530                 535                 540
Cys Asp Arg Val Asp Gln Leu Thr Ala Gln Leu Ala Asp Leu Ala Ala
545                 550                 555                 560
Arg Gly Glu Gly Glu Ser Pro Gln Ala Arg Ala Leu Ala Ser Gln Leu
                    565                 570                 575
Gln Asp Ser Leu Lys Asp Leu Lys Ala Arg Met Gln Glu Ala Met Thr
                580                 585                 590
Gln Glu Val Ser Asp Val Phe Ser Asp Thr Thr Thr Pro Ile Lys Leu
                595                 600                 605
Leu Ala Val Ala Ala Thr Ala Pro Pro Asp Ala Pro Asn Arg Glu Glu
                610                 615                 620
Val Phe Asp Glu Arg Ala Ala Asn Phe Glu Asn His Ser Gly Lys Leu
625                 630                 635                 640
Gly Ala Thr Ala Glu Lys Ala Ala Ala Val Gly Thr Ala Asn Lys Ser
                    645                 650                 655
Thr Val Glu Gly Ile Gln Ala Ser Val Lys Thr Ala Arg Glu Leu Thr
                    660                 665                 670
Pro Gln Val Val Ser Ala Ala Arg Ile Leu Leu Arg Asn Pro Gly Asn
                    675                 680                 685
Gln Ala Ala Tyr Glu His Phe Glu Thr Met Lys Asn Gln Trp Ile Asp
                    690                 695                 700
Asn Val Glu Lys Met Thr Gly Leu Val Asp Glu Ala Ile Asp Thr Lys
705                 710                 715                 720
Ser Leu Leu Asp Ala Ser Glu Glu Ala Ile Lys Lys Asp Leu Asp Lys
                    725                 730                 735
Cys Lys Val Ala Met Ala Asn Ile Gln Pro Gln Met Leu Val Ala Gly
                    740                 745                 750
Ala Thr Ser Ile Ala Arg Arg Ala Asn Arg Ile Leu Leu Val Ala Lys
                    755                 760                 765
Arg Glu Val Glu Asn Ser Glu Asp Pro Lys Phe Arg Glu Ala Val Lys
                    770                 775                 780
Ala Ala Ser Asp Glu Leu Ser Lys Thr Ile Ser Pro Met Val Met Asp
785                 790                 795                 800
Ala Lys Ala Val Ala Gly Asn Ile Ser Asp Pro Gly Leu Gln Lys Ser
                    805                 810                 815
Phe Leu Asp Ser Gly Tyr Arg Ile Leu Gly Ala Val Ala Lys Val Arg
                    820                 825                 830
Glu Ala Phe Gln Pro Gln Glu Pro Asp Phe Pro Pro Pro Pro Pro Asp
                    835                 840                 845
Leu Glu Gln Leu Arg Leu Thr Asp Glu Leu Ala Pro Pro Lys Pro Pro
                    850                 855                 860
Leu Pro Glu Gly Glu Val Pro Pro Arg Pro Pro Pro Glu Glu
865                 870                 875                 880
Lys Asp Glu Glu Phe Pro Glu Gln Lys Ala Gly Glu Val Ile Asn Gln
                    885                 890                 895
```

-continued

```
Pro Met Met Met Ala Ala Arg Gln Leu His Asp Glu Ala Arg Lys Trp
        900             905             910
Ser Ser Lys Gly Asn Asp Ile Ile Ala Ala Ala Lys Arg Met Ala Leu
        915             920             925
Leu Met Ala Glu Met Ser Arg Leu Val Arg Gly Gly Ser Gly Thr Lys
    930             935             940
Arg Ala Leu Ile Gln Cys Ala Lys Asp Ile Ala Lys Ala Ser Asp Glu
945             950             955             960
Val Thr Arg Leu Ala Lys Glu Val Ala Lys Gln Cys Thr Asp Lys Arg
            965             970             975
Ile Arg Thr Asn Leu Leu Gln Val Cys Glu Arg Ile Pro Thr Ile Ser
            980             985             990
Thr Gln Leu Lys Ile Leu Ser Thr Val Lys Ala Thr Met Leu Gly Arg
        995             1000            1005
Thr Asn Ile Ser Asp Glu Glu Ser Glu Gln Ala Thr Glu Met Leu
    1010            1015            1020
Val His Asn Ala Gln Asn Leu Met Gln Ser Val Lys Glu Thr Val
    1025            1030            1035
Arg Glu Ala Glu Ala Ala Ser Ile Lys Ile Arg Thr Asp Ala Gly
    1040            1045            1050
Phe Thr Leu Arg Trp Val Arg Lys Thr Pro Trp Tyr Gln
    1055            1060            1065
```

METHODS AND SYSTEMS FOR DISTINGUISHING IRRITABLE BOWEL SYNDROME FROM INFLAMMATORY BOWEL DISEASE AND CELIAC DISEASE

CROSS-REFERENCE TO RELATED APPLICATIONS

This application is a continuation of U.S. patent application Ser. No. 14/878,416 filed Oct. 8, 2015, now U.S. Pat. No. 10,132,814, which includes a claim of priority under 35 U.S.C. § 119(e) to U.S. provisional patent application No. 62/061,877, filed Oct. 9, 2014, and U.S. provisional patent application No. 62/085,825, filed Dec. 1, 2014, the entirety of which are hereby incorporated by reference.

FIELD OF INVENTION

This invention relates to irritable bowel syndrome, the diagnosis and treatments thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Irritable bowel syndrome (IBS) is the most commonly diagnosed condition in gastroenterology with reported prevalence rates of approximately 15% of the population. Over the last 30 years, the diagnosis of IBS has been based on clinical criteria. This is due to a poor understanding of the pathophysiology of this condition.

Two microbial concepts have emerged in the pathogenesis of IBS. The first suggests that IBS symptoms appear to be related to alterations in small bowel microbial flora. The evidence for this is based on breath testing, small bowel culture, small bowel flora deep sequencing, and the clinical response to the gut-specific antibiotic, rifaximin. The second microbial concept is that a subset of subjects develops IBS following an episode of acute gastroenteritis (AGE). Meta-analyses of classic outbreaks suggest that the rate of IBS developing after AGE is approximately 10%.

IBS is a condition that results in chronic changes in bowel function including diarrhea, constipation and alternating patterns, as well as abdominal symptoms including pain and bloating. Because the symptoms of IBS can overlap with organic diseases such as IBD and celiac disease, the diagnosis of IBS is often made after excluding organic diseases. In a recent multinational initiative, IBS experts agreed that these subjects suffer from significant changes in bowel habit and bloating as principal symptoms. In the absence of a clear pathophysiology of IBS, identification of subjects is based on a "diagnosis of exclusion" approach. This approach involves a great deal of expense and morbidity to patients with IBS, particularly those with D-IBS, including frequent body imaging, endoscopy and blood testing to rule out alternative organic explanations for their symptoms.

While the Rome criteria have been valuable in the standardization of IBS recruitment for clinical trials, these criteria still rely on a "diagnosis of exclusion" approach as they are non-specific. For example, the majority of subjects with Crohn's disease or ulcerative colitis satisfy the Rome Criteria. The Rome II Criteria were further helpful in defining IBS based on predominant bowel pattern such as diarrhea and constipation predominant forms. This approach led to drug pipelines for IBS treatment based on controlling symptoms in IBS. Prokinetics and secretagogues have been developed for C-IBS and anti-kinetics for D-IBS. However, these therapies are not based on causative mechanism of IBS and are instead based on symptom control. As a result, they can result in creating opposite symptoms.

While the diagnosis of celiac disease has been greatly enhanced by the measurement of serum tissue transglutaminase, there remains a need for biomarkers that distinguish IBS from IBD in the workup of chronic diarrhea. There remains a need in the art for methods, assays and systems to diagnose IBS and to distinguish IBS from other GI ailments such as IBD and celiac disease.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method of distinguishing irritable bowel syndrome (IBS) from inflammatory bowel disease (IBD), celiac disease, or both, comprising: obtaining a biological sample from a subject desiring a diagnosis to distinguish IBS from IBD, celiac disease, or both; detecting in the biological sample, levels of anti-vinculin and anti-CdtB antibodies; and making a diagnosis of IBS if the level of anti-vinculin antibodies is higher than an established control level of anti-vinculin antibodies, the level of anti-CdtB antibodies is higher than an established control level of anti-CdtB antibodies, or both levels of anti-vinculin antibodies and anti-CdtB antibodies are higher than the established control levels of anti-vinculin antibodies and anti-CdtB antibodies, or making a diagnosis of IBD, suspicion of IBD, celiac disease or suspicion of celiac disease if the level of anti-vinculin antibodies is not higher than the established control level of anti-vinculin antibodies and the level of anti-CdtB antibodies is not higher than the established control level of anti-CdtB antibodies.

In various embodiments, the biological sample can be whole blood, serum, or plasma.

In various embodiments, detecting in the biological sample can comprise using enzyme-linked immunosorbent assay (ELISA). In various embodiments, detecting in the biological sample can comprise using immunohistochemistry, flow cytometry, fluorescence in situ hybridization (FISH), radioimmuno assays, or affinity purification.

In various embodiments, the anti-vinculin antibodies can be capable of binding specifically to an epitope on vinculin or SEQ ID NO:7.

In various embodiments, the anti-CdtB antibodies can be capable of binding specifically to an epitope on CdtB of *Campylobacter jejuni* or SEQ ID NO:5.

In certain embodiments, the diagnosis of IBS can be made if the level of anti-vinculin antibodies is higher than the established control level of anti-vinculin antibodies. In certain embodiments, the diagnosis of IBS can be made if the level of anti-CdtB antibodies is higher than the established control level of anti-CdtB antibodies. In various embodiments, the diagnosis of IBS can be made if both levels of anti-vinculin antibodies and anti-CdtB antibodies are higher than the established control levels of anti-vinculin antibodies and anti-CdtB antibodies.

In various embodiments, the established control level of anti-vinculin antibodies, anti-CdtB antibodies, or both can be an optical density measurement.

Various embodiments of the present invention provide for a method of selecting a treatment for irritable bowel syndrome (IBS), inflammatory bowel disease (IBD), or celiac disease, comprising: obtaining a biological sample from a subject desiring a diagnosis to distinguish IBS from IBD, celiac disease, or both; detecting in the biological sample, levels of anti-vinculin and anti-CdtB antibodies; making a diagnosis of IBS if the level of anti-vinculin antibodies is higher than an established control level of anti-vinculin antibodies, the level of anti-CdtB antibodies is higher than an established control level of anti-CdtB antibodies, or both levels of anti-vinculin antibodies and anti-CdtB antibodies are higher than the established control levels of anti-vinculin antibodies and anti-CdtB antibodies, or making a diagnosis of IBD, suspicion of IBD, celiac disease or suspicion of celiac disease if the level of anti-vinculin antibodies is not higher than the established control level of anti-vinculin antibodies and the level of anti-CdtB antibodies is not higher than the established control level of anti-CdtB antibodies; and selecting an IBS treatment if IBS is diagnosed, selecting an IBD treatment if IBD is diagnosed or suspected, or selecting a celiac treatment if celiac disease is diagnosed or suspected.

In various embodiments, the biological sample can be whole blood, serum, or plasma.

In various embodiments, detecting in the biological sample can comprise using enzyme-linked immunosorbent assay (ELISA). In various embodiments, detecting in the biological sample can comprise using immunohistochemistry, flow cytometry, fluorescence in situ hybridization (FISH), radioimmuno assays, or affinity purification.

In various embodiments, the anti-vinculin antibodies can be capable of binding specifically to an epitope on vinculin or SEQ ID NO:7.

In various embodiments, the anti-CdtB antibodies can be capable of binding specifically to an epitope on CdtB of *Campylobacter jejuni* or SEQ ID NO:5.

In various embodiments, the established control level of anti-vinculin antibodies, anti-CdtB antibodies, or both can be an optical density measurement.

In certain embodiments, the diagnosis of IBS can be made if the level of anti-vinculin antibodies is higher than the established control level of anti-vinculin antibodies. In certain embodiments, the diagnosis of IBS can be made if the level of anti-CdtB antibodies is higher than the established control level of anti-CdtB antibodies. In certain embodiments, the diagnosis of IBS can be made if both levels of anti-vinculin antibodies and anti-CdtB antibodies are higher than the established control levels of anti-vinculin antibodies and anti-CdtB antibodies.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1A:
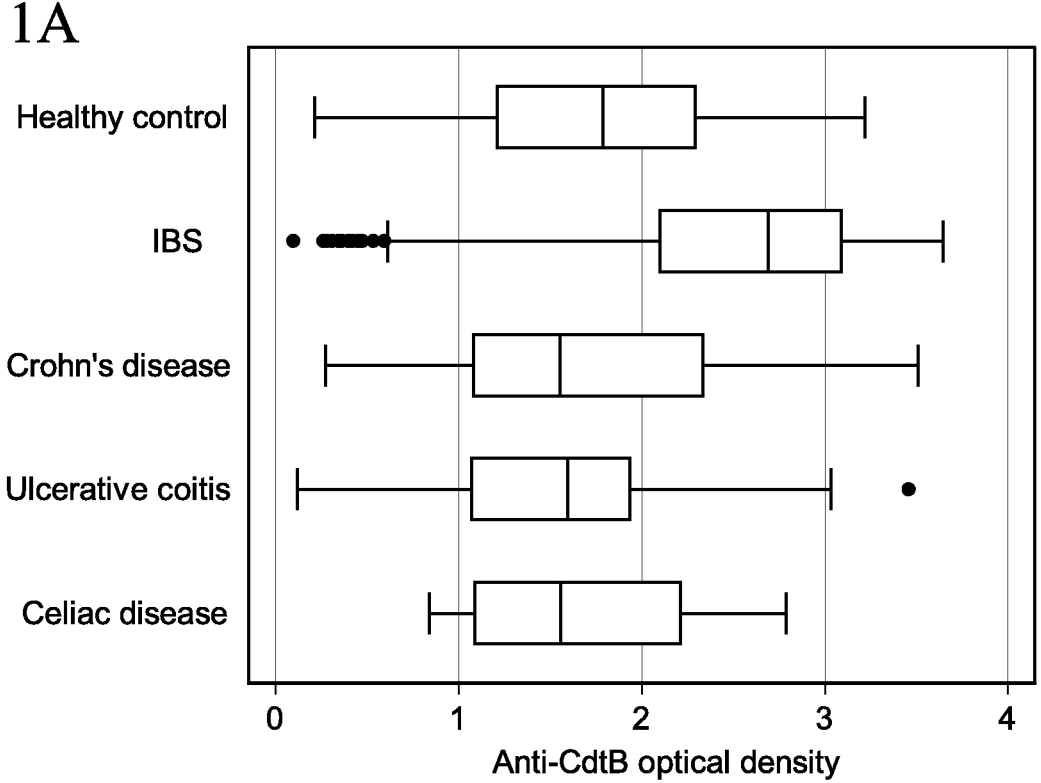
FIG. 1A depicts comparison of anti-CdtB antibody OD among the groups in accordance with various embodiments of the present invention.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, N.Y. 2006); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* 2$^{nd}$ ed. (Cold Spring Harbor Press, Cold Spring Harbor N.Y., 2013); Kohler and Milstein, (1976) *Eur. J. Immunol.* 6: 511;

Queen et al. U.S. Pat. No. 5,585,089; and Riechmann et al., *Nature* 332: 323 (1988); U.S. Pat. No. 4,946,778; Bird, *Science* 242:423-42 (1988); Huston et al., *Proc. Natl. Acad. Sci. USA* 85:5879-5883 (1988); Ward et al., *Nature* 334: 544-54 (1989); Tomlinson I. and Holliger P. (2000) *Methods Enzymol*, 326, 461-479; Holliger P. (2005) *Nat. Biotechnol.* September; 23(9): 1126-36).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus adult and newborn subjects, as well as fetuses, whether male or female, are intended to be including within the scope of this term.

"Treatment" and "treating," as used herein refer to both therapeutic treatment and prophylactic or preventative measures (e.g., to reduce the likelihood of having the condition or disease condition), wherein the object is to prevent or slow down (lessen) the targeted pathologic condition or disorder even if the treatment is ultimately unsuccessful. Those in need of treatment include those already with the condition or disorder as well as those prone to have the condition or disorder or those in whom the condition or disorder is to be prevented (e.g., reducing the likelihood of having the condition or disorder).

"Antibody" or "antibodies" as used herein include polyclonal antibodies, monoclonal antibodies, antibody variants such as single chain (recombinant) Fv, human antibodies, humanized antibodies, chimeric antibodies, and immunologically active fragments of antibodies.

""Binds specifically" as used herein refers to the act of an antibody binding to its antigen and is intended to exclude low-level, non-specific binding that may occur between random proteins. "Binds specifically" as used herein is not intended and does not imply that the antibody will not bind to any protein other than the proteins or polypeptides as disclosed herein since antibodies can cross-react with any protein that includes the relevant epitope.

"Significantly higher" as used herein relating to reference or control amounts refers to a statistically significant amount higher than the reference or control amount.

A newly validated animal model of post-infectious IBS (PI-IBS) based on infection with *Campylobacter jejuni* suggests that AGE precipitates PI-IBS, leading to significant alterations in small bowel microbial colonization. Using this model, it was determined that the development of IBS-like phenotypes in these animals was dependent on a specific toxin, cytolethal distending toxin B (CdtB). Significantly, the development of IBS-like phenotypes in this animal model was mitigated in the absence of CdtB. In a subsequent series of experiments, we found that, through molecular mimicry, host antibodies to CdtB react with the host protein vinculin in the neuromuscular apparatus of the gut. The presence of circulating antibodies to CdtB and vinculin in the animal model is associated with the development of altered gut microbial populations and changes in the gut neuromuscular apparatus, including significant reductions in the numbers of interstitial cells of Cajal (ICC) in the deep muscular plexus.

Based on these new pathophysiologic mechanisms underlying IBS, we assessed the prevalence of anti-CdtB and anti-vinculin antibodies and CdtB in a large cohort of IBS patients and non-IBS controls to validate biomarkers for IBS based on detection of circulating antibodies to vinculin and CdtB in humans.

Described herein, we describe a biomarker for D-IBS based on, without wishing to being bound by any specific theory, a pathophysiologic mechanism of post-infectious IBS and the subsequent development of autoantibodies to vinculin in the host. The test appears specific not only for diagnosing D-IBS but in the workup of chronic diarrhea, can differentiate D-IBS subjects from those with IBD.

While the rate of developing IBS after a single acute gastroenteritis is approximately 10%, military deployment data and mathematical modeling suggest that PI-IBS could account for a large portion of IBS in the US. PI-IBS occurs primarily, though not exclusively, after bacterial infections such as *Campylobacter jejuni, Salmonella, E. coli* and *Shigella*. One toxin commonly produced by all four of these organisms is cytolethal distending toxin, a heterotrimeric complex of three subunits, CdtA, CdtB, and CdtC, of which CdtB is the active subunit.

A validated animal model developed using *C. jejuni* 81-176 has been shown to exhibit an IBS-like phenotype. Significantly, these rats exhibit changes in stool form, small intestinal bacterial overgrowth (SIBO) and the increased rectal intra-epithelial lymphocytes characteristic of humans with IBS. In this model the effects appeared to be due to changes in gut neuroanatomy, with a notable reduction in interstitial cells of Cajal. Further, rats infected with a mutant *C. jejuni* strain lacking CdtB exhibited a significantly mitigated IBS-like phenotype compared to those infected with wild-type *C. jejuni*, suggesting that CdtB was important in the development of IBS in this model. Through a series of immunologic experiments in this model, it was determined that CdtB appeared not to simply be acting through direct toxicity but rather through the cross-reaction of antibodies to CdtB with the host protein vinculin. Levels of circulating antibodies to CdtB and vinculin correlated with the development and levels of SIBO in these animals.

Vinculin is a 117-kDa cytoplasmic actin-binding protein that is a key component of both focal adhesions and adherens junctions, forming the link between integrins or cadherins respectively and the actin cytoskeleton. Furthermore, vinculin appears important in neuronal cell motility and contractility and cardiac formation, as evidenced by the neural tube, myocardial and endocardial defects in vinculin knockout mice, as well as stress-induced cardiomyopathy in heterozygous mutants. In a recently published study, Cdt from *Helicobacter pullorum* has been shown to target vinculin in intestinal epithelial cells, triggering an atypical delocalization of vinculin from focal adhesions coupled with decreased cellular adherence. Another study demonstrated that vinculin is used by the IpA toxin of *Shigella* to achieve cell entry.

Based on the pathophysiologic observations in this animal model, we hypothesized that exposure to CdtB led to detectable immunity to CdtB and autoimmunity to vinculin based on molecular mimicry. In this study, we evaluate whether levels of these antibodies serve as a biomarker for D-IBS in humans for the first time using a large number of IBS and non-IBS patients. We observe that plasma antibodies to vinculin and CdtB were elevated in D-IBS compared to healthy controls, subjects with celiac disease, and subjects with IBD such that the biomarkers appeared to be able to distinguish D-IBS from all non-IBS. Based on ideal cutoff titers, the test has a high specificity for identifying D-IBS compared to IBD. Since tTG is a robust test for celiac disease, in the workup of chronic diarrhea, a real unmet need is a biomarker that could reliably distinguish IBS from IBD. Interestingly anti-CdtB, but not anti-vinculin, was high in celiac disease as well. Another significant unmet need for celiac disease is a test that readily distinguishes functional symptoms from ongoing gluten exposure. Studies suggest that after gluten exposure, IBS is the second most common cause of non-responsive celiac disease, and therefore, a test that could distinguish between these causes of symptoms would be useful clinically.

Based on these results, circulating anti-CdtB and anti-vinculin antibodies are biomarkers for D-IBS and offer some unique perspectives on the pathophysiology of PI-IBS. While not wishing to be bound by any particular theory, first, these are biomarkers based on a mechanism for the development of IBS which may involve alterations to the enteric nervous system and gut motility. Secondly, they represent the first opportunity to make IBS a diagnosis of inclusion rather than a "diagnosis of exclusion". Since not all D-IBS subjects test positive for these biomarkers, it is also possible that these antibodies identify a subgroup of IBS for which a mechanism and therapies could be developed. Finally, it suggests that IBS may have an organic basis. As a biomarker, measurements of anti-vinculin and anti-CdtB antibodies could help to identify D-IBS without excessive investigation and may help to target investigations in those where the test is negative.

While the test has a lower specificity for identifying D-IBS compared to celiac disease, concomitant testing with anti-tTG should compensate for this.

In conclusion, this study validates the presence of anti-vinculin and anti-CdtB as blood based biomarkers that separate D-IBS from IBD and healthy controls using a large scale prospective multicenter trial. Anti-vinculin and anti-CdtB antibodies also appear part of the pathophysiology of post-infectious IBS and may identify a subgroup of D-IBS for directed therapies. Most importantly, this appears to be an important step in determining organic bases for IBS.

Distinguishing IBS from IBD and Celiac Disease

Various embodiments of the present invention provide for methods, assays and systems of distinguishing IBS from IBD and Celiac disease.

The method can comprise providing a biological sample from a subject desiring a diagnosis to distinguish IBS from IBD and Celiac disease, detecting in the biological sample, a presence of anti-vinculin antibodies, and making a diagnosis of IBS if the presence of anti-vinculin antibodies is detected, or making a diagnosis of IBD, suspicion of IBD, Celiac disease or suspicion of Celiac disease if there is an absence of anti-vinculin antibodies. In certain embodiments, the method further comprises analyzing the biological sample for the presence or absence of anti-vinculin antibodies. In certain embodiments, the method further comprises selecting an IBS treatment if IBS is diagnosed, selecting an IBD treatment if IBD is diagnosed or suspected, or selecting a Celiac disease treatment of Celiac disease is diagnosed or suspected.

In various embodiments, the method can comprise providing a biological sample from a subject desiring a diagnosis to distinguish IBS from IBD and Celiac disease, detecting in the biological sample, a level of anti-vinculin antibodies, and making a diagnosis of IBS if the level of anti-vinculin antibodies is higher than an established control level, or making a diagnosis of IBD, suspicion of IBD, Celiac disease, or suspicion of Celiac disease if the level of anti-vinculin antibodies is equal or lower than the established control level. In various embodiments, the established control level is a level of anti-vinculin antibodies within two standard deviations of anti-vinculin antibody levels from healthy subjects without IBS, IBD, Celiac disease or combinations thereof. In certain embodiments, the method further comprises analyzing the biological sample for a level of anti-vinculin antibodies.

In various embodiments, the method can comprise providing a biological sample from a subject desiring a diagnosis to distinguish IBS from IBD and Celiac disease, detecting in the biological sample, a level of anti-vinculin antibodies, and making a diagnosis of IBS if the level of anti-vinculin antibodies is significantly higher than an established control level, or making a diagnosis of IBD, suspicion of IBD, Celiac disease or suspicion of Celiac disease if the level of anti-vinculin antibodies is not significantly higher than the established control level. In various embodiments, the established control level is a level of anti-vinculin antibodies from subjects without IBS, IBD, Celiac disease or combinations thereof. In certain embodiments, the method further comprises analyzing the biological sample for a level of anti-vinculin antibodies. In certain embodiments, the method further comprises selecting an IBS treatment if IBS is diagnosed, selecting an IBD treatment if IBD is diagnosed or suspected, or selecting a Celiac disease treatment of Celiac disease is diagnosed or suspected.

The method can comprise providing a biological sample from a subject desiring a diagnosis to distinguish IBS from IBD and Celiac disease, detecting in the biological sample, a presence of anti-CdtB antibodies, and making a diagnosis of IBS if the presence of anti-CdtB antibodies is detected, or making a diagnosis of IBD, suspicion of IBD, Celiac disease or suspicion of Celiac disease if there is an absence of anti-CdtB antibodies. In certain embodiments, the method further comprises analyzing the biological sample for the presence or absence of anti-CdtB antibodies. In certain embodiments, the method further comprises selecting an IBS treatment if IBS is diagnosed, selecting an IBD treatment if IBD is diagnosed or suspected, or selecting a Celiac treatment if Celiac disease is diagnosed or suspected.

In various embodiments, the method can comprise providing a biological sample from a subject desiring a diagnosis to distinguish IBS from IBD and Celiac disease, detecting in the biological sample, a level of anti-CdtB antibodies, and making a diagnosis of IBS if the level of anti-CdtB antibodies is higher than an established control level, or making a diagnosis of IBD, suspicion of IBD, Celiac disease or suspicion of Celiac disease if the level of anti-CdtB antibodies is equal or lower than the established control level. In various embodiments, the established control level is a level of anti-CdtB antibodies within two standard deviations of anti-CdtB antibody levels from healthy subjects without IBS, IBD, Celiac disease or combinations thereof. In certain embodiments, the method further comprises analyzing the biological sample for a level of anti-CdtB antibodies. In certain embodiments, the method further comprises selecting an IBS treatment if IBS is diagnosed, selecting an IBD treatment if IBD is diagnosed or suspected, or selecting a Celiac disease treatment of Celiac disease is diagnosed or suspected.

In various embodiments, the method can comprise providing a biological sample from a subject desiring a diagnosis to distinguish IBS from IBD and Celiac disease, detecting in the biological sample, a level of anti-CdtB antibodies, and making a diagnosis of IBS if the level of anti-CdtB antibodies is significantly higher than an established control level, or making a diagnosis of IBD, suspicion of IBD, Celiac disease or suspicion of Celiac disease if the level of anti-CdtB antibodies is not significantly higher than the established control level. In various embodiments the established control level is a level of anti-CdtB antibodies from subjects without IBS, IBD, Celiac disease or combinations thereof. In certain embodiments, the method further comprises analyzing the biological sample for a level of anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish IBS from IBD and Celiac disease, detecting in the biological sample, a presence of anti-vinculin and anti-CdtB antibodies, and making a diagnosis of IBS if the presence of anti-vinculin and anti-CdtB antibodies are detected, or making a diagnosis of IBD, suspicion of IBD, Celiac disease or suspicion of Celiac disease if there are an absence of anti-vinculin and anti-CdtB antibodies. In certain embodiments, the method further comprises analyzing the biological sample for the presence or absence of anti-vinculin and anti-CdtB antibodies. In certain embodiments, the method further comprises selecting an IBS treatment if IBS is diagnosed, selecting an IBD treatment if IBD is diagnosed or suspected, or selecting a Celiac treatment if Celiac disease is diagnosed or suspected.

In various embodiments, the method can comprise providing a biological sample from a subject desiring a diagnosis to distinguish IBS from IBD and Celiac disease, detecting in the biological sample, a level of anti-vinculin and anti-CdtB antibodies, and making a diagnosis of IBS if the levels of anti-vinculin and anti-CdtB antibodies are higher than an established control level, or making a diagnosis of IBD, suspicion of IBD, Celiac disease or suspicion of Celiac disease if the levels of anti-vinculin and anti-CdtB antibodies are equal or lower than the established control levels. In various embodiments, the established control levels are levels of anti-vinculin and anti-CdtB antibodies within two standard deviations of anti-vinculin and anti-CdtB antibody levels from healthy subjects without IBS, IBD, Celiac disease or combinations thereof. In certain embodiments, the method further comprises analyzing the biological sample levels of anti-vinculin and anti-CdtB antibodies. In certain embodiments, the method further comprises selecting an IBS treatment if IBS is diagnosed, selecting an IBD treatment if IBD is diagnosed or suspected, or selecting a Celiac disease treatment if Celiac disease is diagnosed or suspected.

In various embodiments, the method can comprise providing a biological sample from a subject desiring a diagnosis to distinguish between IBS and IBD, detecting in the biological sample, a level of anti-vinculin and anti-CdtB antibodies, and making a diagnosis of IBS if the level of anti-vinculin and anti-CdtB antibodies is significantly higher than an established control level, or making a diagnosis of IBD, suspicion of IBD, Celiac disease or suspicion of Celiac disease if the level of anti-vinculin and anti-CdtB antibodies is not significantly higher than the established control levels. In various embodiments the established control levels are levels of anti-vinculin and anti-CdtB antibodies from subjects without IBS, IBD, Celiac disease or combinations thereof. In certain embodiments, the method further comprises analyzing the biological sample for levels of anti-vinculin and anti-CdtB antibodies. In certain embodiments, the method further comprises selecting an IBS treatment if IBS is diagnosed, selecting an IBD treatment if IBD is diagnosed or suspected, or selecting a Celiac disease treatment if Celiac disease is diagnosed or suspected.

In various embodiments, the system can comprise an isolated biological sample from a subject desiring distinguishing IBS from IBD and Celiac disease, and an assay for detecting in the biological sample, a presence of an anti-vinculin antibody or a level of anti-vinculin antibody to distinguish IBS from IBD and Celiac disease.

In various embodiments, the IBS can be C-IBS, D-IBS, A-IBS (also known as M-IBS), or post-infectious irritable bowel syndrome (PI-IBS). In particular embodiments, the IBS is D-IBS.

In various embodiments, if a diagnosis or suspicion of IBD is made, it can be further correlated with IBD symptoms to further confirm IBD. In other embodiments, additional IBD testing can be done to further confirm IBD.

In various embodiments, if a diagnosis or suspicion of Celiac disease is made, it can be further correlated with Celiac disease symptoms to further confirm Celiac disease. In other embodiments, additional celiac disease testing can be done to further confirm Celiac disease; for example, measurement of serum tissue transglutaminase.

In various embodiments the assay is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample if the biological sample comprises the anti-vinculin antibody (if anti-vinculin antibodies are not present, then the first reagent will not react the biological sample, but the first reagent is still present in the assay), a second reagent (e.g., secondary antibody) to react with the anti-vinculin antibody or a second reagent to react with the first reagent, and a substrate. In various embodiments, the first reagent is vinculin or a fragment thereof. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of IBS if the presence of anti-vinculin antibodies, anti-CdtB antibodies or both is detected, or determining the presence or likely presence of IBD or Celiac disease if there is an absence of anti-vinculin antibodies, anti-CdtB antibodies or both. In various embodiments, the machine is a computer. In various embodiments, the computer comprises a display element for displaying whether the patient likely has IBS, IBD or Celiac disease.

In various embodiments, the system further comprises a machine for determining a presence or likely presence of IBS if the level of anti-vinculin antibodies, anti-CdtB antibodies, or both is higher than an established control level(s), or determining a presence or likely presence of IBD if the level of anti-vinculin antibodies, anti-CdtB antibodies, or both is equal or lower than the established control level(s). In various embodiments, the established control level is a level of anti-vinculin antibodies, anti-CdtB antibodies, or both within two standard deviations of the level of anti-vinculin antibodies, anti-CdtB antibodies, or both from healthy subjects without IBS, IBD, Celiac disease or combinations thereof. In certain embodiments, the method further comprises analyzing the biological sample for a level of anti-vinculin antibodies.

In various embodiments, the system further comprises a machine for determining a presence or likely presence of IBS if the level of anti-vinculin antibodies, anti-CdtB antibodies, or both is significantly higher than an established control level, or determining a presence or likely presence of IBD if the level of anti-vinculin antibodies, anti-CdtB antibodies, or both is not significantly higher than the established control level. In various embodiments the established control level is a level of anti-vinculin antibodies, anti-CdtB antibodies, or both from healthy subjects without IBS, IBD, Celiac disease or combinations thereof. In certain embodiments, the method further comprises analyzing the biological sample for a level of anti-vinculin antibodies, anti-CdtB antibodies, or both.

In various embodiments, the machine is a computer. In various embodiments, the computer comprises a display element for displaying whether the patient likely has IBS, IBD or Celiac disease.

Various embodiments provide for treating IBS in a subject who may have IBS, IBD or Celiac disease. The method comprises providing an IBS therapy and administering the IBS therapy to a subject diagnosed with IBS using the methods of the present invention. That is, the subject has been diagnosed with IBS via the detection of the presence of anti-vinculin and anti-CdtB antibodies in accordance with the methods of the present invention as discussed herein.

In various embodiments, the IBS therapy is a therapy as described herein. In various embodiments, the IBS therapy comprises administering a course of antibiotic therapy to treat IBS. In various embodiments, the IBS therapy is an available therapy in the prior art. In various embodiments, the IBS therapy is a course of antibiotic therapy as described herein.

In various embodiments, the IBS treated can be C-IBS, D-IBS, A-IBS (also known as M-IBS), or post-infectious irritable bowel syndrome (PI-IBS). In particular embodiments, the IBS is D-IBS.

Distinguishing Between IBS and IBD

Various embodiments of the present invention provide for methods, assays and systems of distinguishing between IBS and IBD.

The method can comprise providing a biological sample from a subject desiring a diagnosis to distinguish between IBS and IBD, detecting in the biological sample, a presence of anti-vinculin antibodies, and making a diagnosis of IBS if the presence of anti-vinculin antibodies is detected, or making a diagnosis of IBD or suspicion of IBD if there is an absence of anti-vinculin antibodies. In certain embodiments, the method further comprises analyzing the biological sample for the presence or absence of anti-vinculin antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a level of anti-vinculin antibodies, and making a diagnosis of IBS if the level of anti-vinculin antibodies is higher than an established control level, or making a diagnosis of IBD or suspicion of IBD if the level of anti-vinculin antibodies is equal or lower than the established control level. In various embodiments, the established control level is a level of anti-vinculin antibodies within two standard deviations of anti-vinculin antibody levels from healthy subjects without IBS, IBD or both. In certain embodiments, the method further comprises analyzing the biological sample for a level of anti-vinculin antibodies.

In various embodiments, the method can comprise providing a biological sample from a subject desiring a diagnosis to distinguish between IBS and IBD, detecting in the biological sample, a level of anti-vinculin antibodies, and making a diagnosis of IBS if the level of anti-vinculin antibodies is significantly higher than an established control level, or making a diagnosis of IBD or suspicion of IBD if the level of anti-vinculin antibodies is not significantly higher than the established control level. In various embodiments, the established control level is a level of anti-vinculin antibodies from subjects without IBS, IBD or both. In certain embodiments, the method further comprises analyzing the biological sample for a level of anti-vinculin antibodies. In certain embodiments, the method further comprises selecting an IBS treatment if IBS is diagnosed, or selecting an IBD treatment if IBD is diagnosed or suspected.

The method can comprise providing a biological sample from a subject desiring a diagnosis to distinguish between IBS and IBD, detecting in the biological sample, a presence of anti-CdtB antibodies, and making a diagnosis of IBS if the presence of anti-CdtB antibodies is detected, or making a diagnosis of IBD or suspicion of IBD if there is an absence of anti-CdtB antibodies. In certain embodiments, the method further comprises analyzing the biological sample for the presence or absence of anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a level of anti-CdtB antibodies, and making a diagnosis of IBS if the level of anti-CdtB antibodies is higher than an established control level, or making a diagnosis of IBD or suspicion of IBD if the level of anti-CdtB antibodies is equal or lower than the established control level. In various embodiments, the established control level is a level of anti-CdtB antibodies within two standard deviations of anti-CdtB antibody levels from healthy subjects without IBS, IBD or both. In certain embodiments, the method further comprises analyzing the biological sample for a level of anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a level of anti-CdtB antibodies, and making a diagnosis of IBS if the level of anti-CdtB antibodies is significantly higher than an established control level, or making a diagnosis of IBD or suspicion of IBD if the level of anti-CdtB antibodies is not significantly higher than the established control level. In various embodiments the established control level is a level of anti-CdtB antibodies from subjects without IBS, IBD or both. In certain embodiments, the method further comprises analyzing the biological sample for a level of anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a presence of anti-vinculin and anti-CdtB antibodies, and making a diagnosis of IBS if the presence of anti-vinculin and anti-CdtB antibodies is detected, or making a diagnosis of IBD or suspicion of IBD if there are an absence of anti-vinculin and anti-CdtB antibodies. In certain embodiments, the method further comprises analyzing the biological sample for the presence or absence of anti-vinculin and anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a level of anti-vinculin and anti-CdtB antibodies, and making a diagnosis of IBS if the levels of anti-vinculin and anti-CdtB antibodies are higher than an established control level, or making a diagnosis of IBD or suspicion of IBD if the levels of anti-vinculin and anti-CdtB antibodies are equal or lower than the established control levels. In various embodiments, the established control levels are levels of anti-vinculin and anti-CdtB antibodies within two standard deviations of anti-vinculin and anti-CdtB antibody levels from healthy subjects without IBS, IBD or both. In certain embodiments, the method further comprises analyzing the biological sample levels of anti-vinculin and anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a level of anti-vinculin and anti-CdtB antibodies, and making a diagnosis of IBS if the level of anti-vinculin and anti-CdtB antibodies is significantly higher than an established control level, or making a diagnosis of IBD or suspicion of IBD if the level of anti-vinculin and anti-CdtB antibodies is not significantly higher than the established control levels. In various embodiments the established control levels are levels of anti-vinculin and anti-CdtB antibodies from subjects without IBS, IBD or both. In certain embodiments, the method further comprises analyzing the biological sample for levels of anti-vinculin and anti-CdtB antibodies. In certain embodiments, the method further comprises selecting an IBS treatment if IBS is diagnosed, or selecting an IBD treatment if IBD is diagnosed or suspected.

In various embodiments, the system can comprise an isolated biological sample from a subject desiring distinguishing between IBS and IBD, and an assay for detecting in the biological sample, a presence of an anti-vinculin antibody or a level of anti-vinculin antibody to distinguish between IBS and IBD.

In various embodiments, the IBS can be C-IBS, D-IBS, A-IBS (also known as M-IBS), or post-infectious irritable bowel syndrome (PI-IBS). In particular embodiments, the IBS is D-IBS.

In various embodiments, if a diagnosis or suspicion of IBD is made, it can be further correlated with IBD symptoms to further confirm IBD. In other embodiments, additional IBD testing can be done to further confirm IBD.

In various embodiments the assay is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample if the biological sample comprises the anti-vinculin antibody (if anti-vinculin antibodies are not present, then the first reagent will not react the biological sample, but the first reagent is still present in the assay), a second reagent (e.g., secondary antibody) to react with the anti-vinculin antibody or a second reagent to react with the first reagent, and a substrate. In various embodiments, the first reagent is vinculin or a fragment thereof. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of IBS if the presence of anti-vinculin antibodies, anti-CdtB antibodies or both is detected, or determining the presence or likely presence of IBD if there is an absence of anti-vinculin antibodies, anti-CdtB antibodies or both. In various embodiments, the machine is a computer. In various embodiments, the computer comprises a display element for displaying whether the patient likely has IBS or IBD.

In various embodiments, the system further comprises a machine for determining a presence or likely presence of IBS if the level of anti-vinculin antibodies, anti-CdtB antibodies, or both is higher than an established control level(s), or determining a presence or likely presence of IBD if the level of anti-vinculin antibodies, anti-CdtB antibodies, or both is equal or lower than the established control level(s). In various embodiments, the established control level is a level of anti-vinculin antibodies, anti-CdtB antibodies, or both within two standard deviations of the level of anti-vinculin antibodies, anti-CdtB antibodies, or both from healthy subjects without IBS, IBD or both. In certain embodiments, the method further comprises analyzing the biological sample for a level of anti-vinculin antibodies.

In various embodiments, the system further comprises a machine for determining a presence or likely presence of IBS if the level of anti-vinculin antibodies, anti-CdtB antibodies, or both is significantly higher than an established control level, or determining a presence or likely presence of IBD if the level of anti-vinculin antibodies, anti-CdtB antibodies, or both is not significantly higher than the established control level. In various embodiments the established control level is a level of anti-vinculin antibodies, anti-CdtB antibodies, or both from healthy subjects without IBS, IBD or both. In certain embodiments, the method further comprises analyzing the biological sample for a level of anti-vinculin antibodies, anti-CdtB antibodies, or both.

In various embodiments, the machine is a computer. In various embodiments, the computer comprises a display element for displaying whether the patient likely has IBS or IBD.

Diagnosis of IBS

Various embodiments provide for methods, assays and systems of diagnosing or identifying IBS in a subject.

In various embodiments, the method comprises: providing a biological sample from a subject desiring diagnosis of IBS, detecting in the biological sample, a presence of anti-vinculin and anti-CdtB antibodies, and determining a presence or likely presence of IBS if the presence of anti-vinculin and anti-CdtB antibodies are detected, or determining an absence or likely absence of IBS if the absence of anti-vinculin and anti-CdtB antibodies are detected. In certain embodiments, the method further comprises analyzing the biological sample for the presence or absence of anti-vinculin and anti-CdtB antibodies.

In various embodiments, the method comprises: providing a biological sample from a subject desiring diagnosis of IBS, detecting in the biological sample, a level of anti-vinculin and anti-CdtB antibodies, and determining a presence or likely presence of IBS if the level of an anti-vinculin and anti-CdtB antibody is higher than an established control level, or determining the absence or likely absence of IBS if the level of anti-vinculin and anti-CdtB antibody is equal or lower than the established control level. In various embodiments, the established control level is a level of anti-vinculin and anti-CdtB antibodies within two standard deviations of anti-vinculin and anti-CdtB antibody levels from subjects without IBS. In certain embodiments, the method further comprises analyzing the biological sample for a level of anti-vinculin and anti-CdtB antibodies.

In various embodiments, the method comprises: providing a biological sample from a subject desiring diagnosis of IBS, detecting in the biological sample, a level of anti-vinculin and anti-CdtB antibodies, and determining a presence or likely presence of IBS if the level of anti-CdtB antibodies is significantly higher than an established control level, or determining the absence or likely absence of IBS if the level of anti-vinculin and anti-CdtB antibodies is not significantly higher than the established control level. In various embodiments the established control level is a level of anti-vinculin and anti-CdtB antibodies from subjects without IBS. In certain embodiments, the method further comprises analyzing the biological sample for a level of anti-vinculin and anti-CdtB antibodies.

In various embodiments, the method comprises: providing a biological sample from a subject desiring diagnosis of IBS, detecting in the biological sample, a presence of anti-vinculin antibodies, and determining a presence or likely presence of IBS if the presence of anti-vinculin antibodies are detected, or determining an absence or likely absence of IBS if there is an absence of anti-vinculin antibodies. In certain embodiments, the method further comprises analyzing the biological sample for the presence or absence of anti-vinculin antibodies.

In various embodiments, the method comprises: providing a biological sample from a subject desiring diagnosis of IBS, detecting in the biological sample, a level of anti-vinculin antibodies, and determining a presence or likely presence of IBS if the level of an anti-vinculin antibody is higher than an established control level, or determining the absence or likely absence of IBS if the level of an anti-vinculin antibody is equal or lower than the established control level. In various embodiments, the established control level is a level of anti-vinculin antibodies within two standard deviations of anti-vinculin antibody levels from subjects without IBS. In certain embodiments, the method further comprises analyzing the biological sample for a level of anti-vinculin antibodies.

In various embodiments, the method comprises: providing a biological sample from a subject desiring diagnosis of IBS, detecting in the biological sample, a level of anti-vinculin antibodies, and determining a presence or likely presence of IBS if the level of anti-vinculin antibodies is significantly higher than an established control level, or determining the absence or likely absence of IBS if the level of anti-vinculin antibodies is not significantly higher than the established control level. In various embodiments the established control level is a level of anti-vinculin antibodies from subjects without IBS. In certain embodiments, the method further comprises analyzing the biological sample for a level of anti-vinculin antibodies.

In various embodiments, the method comprises: providing a biological sample from a subject desiring diagnosis of IBS, detecting in the biological sample, a presence of anti-CdtB antibodies, and determining a presence or likely presence of IBS if the presence of anti-CdtB antibodies are detected, or determining an absence or likely absence of IBS if there is an absence of anti-CdtB antibodies. In certain embodiments, the method further comprises analyzing the biological sample for the presence or absence of anti-CdtB antibodies.

In various embodiments, the method comprises: providing a biological sample from a subject desiring diagnosis of IBS, detecting in the biological sample, a level of anti-CdtB antibodies, and determining a presence or likely presence of IBS if the level of an anti-CdtB antibody is higher than an established control level, or determining the absence or likely absence of IBS if the level of an anti-CdtB antibody is equal or lower than the established control level. In various embodiments, the established control level is a level of anti-CdtB antibodies within two standard deviations of anti-CdtB antibody levels from subjects without IBS. In certain embodiments, the method further comprises analyzing the biological sample for a level of anti-CdtB antibodies.

In various embodiments, the method comprises: providing a biological sample from a subject desiring diagnosis of IBS, detecting in the biological sample, a level of anti-CdtB antibodies, and determining a presence or likely presence of IBS if the level of anti-CdtB antibodies is significantly higher than an established control level, or determining the absence or likely absence of IBS if the level of anti-CdtB antibodies is not significantly higher than the established control level. In various embodiments the established control level is a level of anti-CdtB antibodies from subjects without IBS. In certain embodiments, the method further comprises analyzing the biological sample for a level of anti-CdtB antibodies.

Not all subjects with the presence of anti-vinculin antibodies and/or anti-CdtB antibodies will have or develop IBS; however, these methods provide an indication on a likelihood of whether the subject has IBS or will develop IBS. A determination of a likely presence of IBS may be further correlated and/or confirmed by other diagnostic methods for IBS, or with symptoms of IBS known in the art. Further, a determination of a likely absence of IBS may also be further correlated and/or confirmed by other diagnostics methods for IBS or symptoms of IBS known in the art to rule out IBS.

In various embodiments, the IBS can be C-IBS, D-IBS, A-IBS (also known as M-IBS), or post-infectious irritable bowel syndrome (PI-IBS). In particular embodiments, the IBS is D-IBS.

In various embodiments, the system comprises: an isolated biological sample from a subject desiring diagnosis of IBS, and an assay for detecting in the biological sample, a presence or level of anti-vinculin and anti-CdtB antibodies.

In various embodiments, the system comprises: an isolated biological sample from a subject desiring diagnosis of IBS, and an assay for detecting in the biological sample, a presence or level of an anti-vinculin antibody.

In various embodiments, the system comprises: an isolated biological sample from a subject desiring diagnosis of IBS, and an assay for detecting in the biological sample, a presence or level of an anti-CdtB antibody.

In various embodiments the assay is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample, a second reagent (e.g., secondary antibody) to react with the anti-vinculin antibody, and a substrate. In various embodiments, the first reagent is vinculin or a fragment thereof, which will react with the anti-vinculin antibody if present in the biological sample. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of IBS if the presence of anti-vinculin antibodies is detected, or determining an absence or likely absence of IBS if the absence of anti-vinculin antibodies is detected. In various embodiments, the machine is a computer. In various embodiments, the computer comprises a display element for displaying whether there is a presence or absence of IBS.

In various embodiments, the system further comprises a machine for determining a presence or likely presence of IBS if the level of anti-vinculin antibodies is higher than an established control level, or determining an absence or likely absence of the IBS if the level of anti-vinculin antibodies is equal or lower than the established control level. In various embodiments, the established control level is a level of anti-vinculin antibodies within two standard deviations of anti-vinculin antibody levels from subjects without IBS. In certain embodiments, the method further comprises analyzing the biological sample for a level of anti-vinculin antibodies.

In various embodiments, the system further comprises a machine for determining a presence or likely presence of IBS if the level of anti-vinculin antibodies is significantly higher than an established control level, or determining an absence or likely absence of IBS if the level of anti-vinculin antibodies is not significantly higher than the established control level. In various embodiments the established control level is a level of anti-vinculin antibodies from subjects without IBS. In certain embodiments, the method further comprises analyzing the biological sample for a level of anti-vinculin antibodies.

In various embodiments, the assay comprises a first reagent to react with the biological sample, a second reagent (e.g., secondary antibody) to react with the anti-CdtB antibody, and a substrate. In various embodiments, the first reagent is CdtB or a fragment thereof, which will react with the anti-CdtB antibody if present in the biological sample. In various embodiments, the second reagent comprises a label to produce a signal to indicate the presence of the anti-CdtB antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-CdtB antibody. In various embodiments, the first reagent comprises a label to produce a signal to indicate the presence of the anti-CdtB antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of IBS if the presence of anti-CdtB antibodies is detected, or determining an absence or likely absence of IBS if the absence of anti-CdtB antibodies is detected. In various embodiments, the machine is a computer. In various embodiments, the computer comprises a display element for displaying whether there is a presence or absence of IBS.

In various embodiments, the system further comprises a machine for determining a presence or likely presence of IBS if the level of anti-CdtB antibodies is higher than an established control level, or determining an absence or likely absence of the IBS if the level of anti-CdtB antibodies is equal or lower than the established control level. In various embodiments, the established control level is a level of anti-CdtB antibodies within two standard deviations of anti-CdtB antibody levels from subjects without IBS. In certain embodiments, the method further comprises analyzing the biological sample for a level of anti-CdtB antibodies.

In various embodiments, the system further comprises a machine for determining a presence or likely presence of IBS if the level of anti-CdtB antibodies is significantly higher than an established control level, or determining an absence or likely absence of IBS if the level of anti-CdtB antibodies is not significantly higher than the established control level. In various embodiments the established control level is a level of anti-CdtB antibodies from subjects without IBS. In certain embodiments, the method further comprises analyzing the biological sample for a level of anti-CdtB antibodies.

In various embodiments, the assay comprises assays (e.g., as described above) for the detection of the levels of anti-vinculin antibodies and anti-CdtB antibodies.

In various embodiments, the determining the presence or level of anti-vinculin antibodies and/or anti-CdtB antibodies comprises adding vinculin or a fragment thereof as discussed herein and/or CdtB or a fragment thereof as discussed herein to a biological sample from a subject desiring a determination regarding IBS, wherein anti-vinculin and/or anti-CdtB antibodies (if present in the biological sample) specifically binds to the vinculin or the fragment thereof and/or the CdtB or the fragment thereof in the biological sample; measuring the levels the anti-vinculin antibodies and the anti-CdtB antibodies in the biological sample; and identifying that the subject has IBS if the levels of the anti-vinculin antibodies is higher than the levels of the anti-CdtB antibodies.

In various embodiments, the assay comprises adding vinculin or a fragment thereof as discussed herein and/or CdtB or a fragment thereof as discussed herein to a biological sample from a subject desiring a determination regarding IBS, wherein anti-vinculin and/or anti-CdtB antibodies (if present in the biological sample) specifically binds to the vinculin or the fragment thereof and/or the CdtB or the fragment thereof in the biological sample; measuring the levels the anti-vinculin antibodies and the anti-CdtB antibodies in the biological sample; and identifying that the subject has IBS if the levels of the anti-vinculin antibodies is higher than the levels of the anti-CdtB antibodies.

Selecting Treatments and Treatments

Various embodiments provide for a method of selecting a therapy for IBS for a subject in need thereof.

In various embodiments, the method comprises: detecting the presence of anti-vinculin antibodies and anti-CdtB antibodies in a subject who desires a diagnosis to distinguish IBS from IBD, Celiac Disease or both; and selecting a therapy to treat IBS.

In various embodiments, the method comprises: detecting the presence of anti-vinculin antibodies in a subject who desires a diagnosis to distinguish IBS from IBD, Celiac Disease or both; and selecting a therapy to treat IBS.

In various embodiments, the method comprises: detecting the presence of anti-CdtB antibodies in a subject who desires a diagnosis to distinguish IBS from IBD, Celiac Disease or both; and selecting a therapy to treat IBS.

Selecting a therapy as used herein, includes but is not limited to selecting, choosing, prescribing, advising, recommending, instructing, or counseling the subject with respect to the treatment.

In various embodiments, the method further comprises administering the therapy to treat IBS. In various embodiments, the therapy is a therapy as described herein. In various embodiments, the available therapy comprises administering a course of antibiotic therapy to treat IBS. In various embodiments, the therapy is an available therapy in the prior art.

In various embodiments, the method comprises: detecting the presence of anti-vinculin antibodies and anti-CdtB antibodies; and selecting a course of antibiotic therapy to treat IBS. In various embodiments, the method further comprises administering the course of antibiotic therapy treat IBS.

In various embodiments, the method comprises: detecting the presence of anti-vinculin antibodies; and selecting a course of antibiotic therapy to treat IBS. In various embodiments, the method further comprises administering the course of antibiotic therapy treat IBS.

In various embodiments, the method comprises: detecting the presence of anti-CdtB antibodies; and selecting a course of antibiotic therapy to treat IBS. In various embodiments, the method further comprises administering the course of antibiotic therapy treat IBS.

In various embodiments, detecting the presence of anti-vinculin antibodies, anti-CdtB antibodies or both can be performed as described by the methods or systems of the present invention.

In various embodiments, the subject can be a subject presenting one or more symptoms of IBS; for example, as discussed herein.

Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole, or a combination thereof. In various embodiments, the antibiotics are a combination of rifaximin and neomycin. In various embodiments, the antibiotics are a combination of rifaximin and doxycycline. In various embodiments, the antibiotics are a combination of rifaximin and metronidazole.

In various embodiments, the antibiotics are non-absorbable antibiotics. Examples of non-absorbable antibiotics include but are not limited to rifaximin, neomycin, Bacitracin, vancomycin, teicoplanin, ramoplanin, and paromomycin.

In various embodiments, the IBS treated can be C-IBS, D-IBS, A-IBS (also known as M-IBS), or post-infectious irritable bowel syndrome (PI-IBS). In particular embodiments, the IBS is D-IBS.

Various embodiments provide for treating IBS in a subject. The method comprises providing an IBS therapy and administering the IBS therapy to a subject diagnosed with IBS using the methods of the present invention. That is, the subject has been diagnosed with IBS via the detection of the presence of anti-vinculin and anti-CdtB antibodies in accordance with the methods of the present invention as discussed herein.

In various embodiments, the IBS therapy is a therapy as described herein. In various embodiments, the IBS therapy comprises administering a course of antibiotic therapy to treat IBS. In various embodiments, the IBS therapy is an available therapy in the prior art. In various embodiments, the IBS therapy is a course of antibiotic therapy as described herein.

In various embodiments, the IBS treated can be C-IBS, D-IBS, A-IBS (also known as M-IBS), or post-infectious irritable bowel syndrome (PI-IBS). In particular embodiments, the IBS is D-IBS.

Optical Density as a Measurement of Antibody Levels

In certain embodiments, optical density (OD) is used to measure the level of anti-vinculin antibodies and/or anti-CDT antibodies. For example, the optical density serves as the established control level in various embodiments. In certain embodiments, when the OD of anti-vinculin antibodies ($OD_V$) is greater than 1.62, 1.86 or 2.23 the subject is determined to have IBS. In various embodiments, when the OD of anti-vinculin antibodies ($OD_V$) is greater than 1.00, 1.25, 1.50, 1.75, 2.00, 2.25, 2.50 2.75 the subject is determined to have IBS. In certain embodiments, these OD numbers are based on a dilution of the biological sample of 1:32 and antigen concentration of 1.2 ug/ml.

In certain embodiments, when the OD of anti-CDT antibodies ($OD_{CDT}$) is greater than 2.48 or 2.79, the subject is determined to have IBS. In various embodiments, when the OD of anti-CDT antibodies ($OD_{CDT}$) is greater than 2.00, 2.25, 2.50, 2.75, 3.00, the subject is determined to have IBS. In certain embodiments, these OD numbers are based on a dilution of the biological sample of 1:512 and antigen concentration of 1.2 ug/ml.

In other embodiments, the $OD_V$ and the $OD_{CDT}$ cutoff points can be determined based on different dilutions of the biological sample and the antigens and are included within the embodiments of the present invention.

In further embodiments, the above determinations may be used to direct the treatment for the subject. In one embodiment, a subject with the likely presence of IBS or a likelihood of having IBS may be treated with one or more therapies for IBS.

One of ordinary skill in the art will be able to select an available treatment for IBS based on the diagnosis of IBS. For example, antibiotics such as rifaximin and neomycin can be used to treat IBS. Particularly, rifaximin can be used to treat diarrhea-predominant IBS, and a rifaximin/neomycin combination can be used to treat constipation-predominant IBS.

Anti-Vinculin Antibodies

In various embodiments, the anti-vinculin antibody detected in these methods or systems is an antibody that binds specifically to vinculin.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising or consisting of 5, 6, 7, 8, 9, 10, 11, 12, 13, 14, 15, 16, 17, 18, 19, 20, 21, or 22 contiguous residues of vinculin.

In various embodiments, the anti-vinculin antibody is an antibody that binds specifically to SEQ ID NO:7.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:7.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:7.

In another embodiment, the anti-vinculin antibody binds specifically to a polypeptide comprising or consisting of 5, 6, 7, 8, 9, 10, 11, 12, 13, 14, 15, 16, 17, 18, 19, 20, 21, or 22 contiguous residues of SEQ ID NO:7.

Contiguous residues of vinculin or SEQ ID NO:7 include those beginning at any amino acid and ending at any amino acid of vinculin or SEQ ID NO:7.

Protein sequence of Vinculin (SEQ ID NO: 7):
MPVFHTRTIESILEPVAQQISHLVIMHEEGEVDGKAIPDLTAPVAAVQAA

VSNLVRVGKETVQTTEDQILKRDMPPAFIKVENACTKLVQAAQMLQSDPY

SVPARDYLIDGSRGILSGTSDLLLTFDEAEVRKIIRVCKGILEYLTVAEV

VETMEDLVTYTKNLGPGMTKMAKMIDERQQELTHQEHRVMLVNSMNTVKE

LLPVLISAMKIFVTTKNSKNQGIEEALKNRNFTVEKMSAEINEIIRVLQL

TSWDEDAWASKDTEAMKRALASIDSKLNQAKGWLRDPSASPGDAGEQAIR

QILDEAGKVGELCAGKERREILGTCKMLGQMTDQVADLRARGQGSSPVAM

QKAQQVSQGLDVLTAKVENAARKLEAMTNSKQSIAKKIDAAQNWLADPNG

GPEGEEQIRGALAEARKIAELCDDPKERDDILRSLGEISALTSKLADLRR

QGKGDSPEARALAKQVATALQNLQTKTNRAVANSRPAKAAVHLEGKIEQA

QRWIDNPTVDDRGVGQAAIRGLVAEGHRLANVMMGPYRQDLLAKCDRVDQ

LTAQLADLAARGEGESPQARALASQLQDSLKDLKARMQEAMTQEVSDVFS

DTTTPIKLLAVAATAPPDAPNREEVFDERAANFENHSGKLGATAEKAAAV

GTANKSTVEGIQASVKTARELTPQVVSAARILLRNPGNQAAYEHFETMKN

QWIDNVEKMTGLVDEAIDTKSLLDASEEAIKKDLDKCKVAMANIQPQMLV

AGATSIARRANRILLVAKREVENSEDPKFREAVKAASDELSKTISPMVMD

-continued
AKAVAGNISDPGLQKSFLDSGYRILGAVAKVREAFQPQEPDFPPPPPDLE

QLRLTDELAPPKPPLPEGEVPPPRPPPPEEKDEEFPEQKAGEVINQPMMM

AARQLHDEARKWSSKGNDIIAAAKRMALLMAEMSRLVRGGSGTKRALIQC

AKDIAKASDEVTRLAKEVAKQCTDKRIRTNLLQVCERIPTISTQLKILST

VKATMLGRTNISDEESEQATEMLVHNAQNLMQSVKETVREAEAASIKIRT

DAGFTLRWVRKTPWYQ

In various embodiments, detecting the presence or absence of the antibody is performed on a biological sample obtained from the subject. In another embodiment, detecting the presence or absence of the antibody is performed on a blood, serum, or stool sample obtained from the subject. One of ordinary skill in the art will readily appreciate methods and systems that can be used to detect the presence or absence of an antibody that binds specifically to vinculin, SEQ ID NO: 7 or a fragment thereof. These methods and systems include but are not limited to ELISA, immunohistochemistry, flow cytometry, fluorescence in situ hybridization (FISH), radioimmuno assays, and affinity purification.

In various embodiments, vinculin, SEQ ID NO: 7 or a fragment thereof (as described above) is used as a substrate or reagent (e.g., collector, trap) to bind anti-vinculin antibodies (if present).

In certain embodiments, detecting the presence or absence of an antibody that binds specifically to vinculin, SEQ ID NO: 7 or a fragment thereof may be performed by contacting vinculin, SEQ ID NO: 7 or a fragment thereof to a biological sample obtained from the subject to isolate the antibody that binds specifically to vinculin, SEQ ID NO: 7 or a fragment thereof, wherein the isolation of the antibody that binds specifically to vinculin, SEQ ID NO: 7 or a fragment thereof indicates the presence of the antibody and the lack of isolation of the antibody that binds specifically to vinculin, SEQ ID NO: 7 or a fragment thereof indicates the lack of the antibody. In various embodiments, the fragment of vinculin or SEQ ID NO: 7 may be the fragments as described herein. As an example, an affinity matrix comprising vinculin, SEQ ID NO: 7 or a fragment thereof can be bound to a solid support; the biological sample can be contacted to the affinity matrix to produce an affinity matrix-antibody complex (if the antibody is present); the affinity matrix-antibody complex can be separated from the remainder of the biological sample; and the antibody can be released from the affinity matrix. In another example, a label (e.g., fluorescent label) can be placed on vinculin, SEQ ID NO: 7 or a fragment thereof; the labeled vinculin, SEQ ID NO: 7 or a fragment thereof can be contacted with a biological sample to allow the antibody (if present) to bind specifically to the labeled vinculin, SEQ ID NO: 7 or a fragment thereof. In various embodiments, the labeled vinculin, SEQ ID NO: 7 or a fragment thereof can be separated out and analyzed for its binding to the antibody.

Anti-CdtB Antibodies

In various embodiments, the anti-CdtB antibody is an antibody that binds specifically to CdtB subunit of CDT. An example of a CdtB amino acid sequence is *Campylobacter jejuni* cytolethal distending toxin B, which has the amino acid sequence (SEQ ID NO: 5). Another example of a CdtB amino acid sequence is *Campylobacter coli* cytolethal distending toxin B, which has the amino acid sequence (SEQ ID NO: 1) and nucleic acid sequence (SEQ ID NO:2).

```
SEQ ID NO: 5:
MKKIICLFLSFNLAFANLENFNVGTWNLQGSSAATESKWSVSVRQLVSGANPLDILMIQEAGTLPRTAT

PTGRHVQQGGTPIDEYEWNLGTLSRPDRVFIYYSRVDVGANRVNLAIVSRMQAEEVIVLPPPTTVSRPI

IGIRNGNDAFFNIHALANGGTDVGAIITAVDAHFANMPQVNWMIAGDFNRDPSTITSTVDRELANRIRV

VFPTSATQASGGTLDYAITGNSNRQQTYTPPLLAAILMLASLRSHIVSDHFPVNFRKF

SEQ ID NO: 1:
MKKIVFLILSFNVLFAALENYNTGTWNLQGSSAATESKWNVSIRQLITGANPMDVLAVQEAGVLPSTAM

MTPRQVQPVGVGIPIHEYIWNLGSVSRPSSVYIYYSRVDVGANRVNLAIVSRVQADEVFVLPPPTVASR

PIIGIRIGNDAFFNIHALASGGNDAGAIVAAVDMFFRNRPDINWMILGDFNRESGALVTLLDPDLRART

RVVVPPSSTQTSGRTIDYAITGNSNTAALYNPPPIVAILALEGLRTFLASDHFPVNFRRP

SEQ ID NO: 2:
atgaaaaaaa tagtattttt gattttaagt tttaatgtat tatttgccgc tttagaaaat    60
tacaacaccg gaacttggaa tttgcaaggc tcatcagctg caactgaaag caaatggaat   120
gttagtataa gacaactcat aaccggtgca aatcctatgg atgttttagc tgttcaagaa   180
gcgggggttt tacctagtac agctatgatg actcctagac aggtacaacc cgtgggcgtg   240
ggtattccta tacatgaata catatggaat ttaggctctg tatcaagacc tagctctgtt   300
tatatatatt attctagagt ggatgtagga gcaaatcgtg tgaatttagc tatcgttagc   360
agagtgcaag cggatgaagt ttttgtttta ccccctccaa cagttgcttc aagacctatt   420
ataggcatac gcataggcaa tgatgctttt ttcaatatac acgctctagc aagtggggga   480
aatgacgcag gagccattgt cgctgctgtg gatatgtttt ttagaaatag acctgatatt   540
aattggatga ttttaggcga ttttaataga gaatcaggcg ccttagtaac cttgctagat   600
```

-continued

```
cctgacttaa gagcacgcac tcgcgtagtt gttccgcctt cttctacgca aacaagtgga    660
agaacgattg attatgctat cactggaaat tccaacactg cagctttata caacccacca    720
ccgatagttg cgattttagc tttagaagga ttaagaacct ttttggcttc agatcatttt    780
cctgtaaatt ttagaagacc ttag                                           804
```

Accordingly, in various embodiments, the antibody binds specifically to SEQ ID NO:5 (CdtB of *C. jejuni*). In various embodiments, the anti-CdtB antibody is an antibody that binds specifically to an amino acid sequence at least 80%, 85%, 90%, 95%, 96%, 97%, 98%, or 99% identical to SEQ ID NO: 5.

In another embodiment, the anti-CdtB antibody is an antibody that binds specifically to SEQ ID NO:1 (CdtB of *C. coli*). In various embodiments, the anti-CdtB antibody is an antibody that binds specifically to an amino acid sequence at least 80%, 85%, 90%, 95%, 96%, 97%, 98%, or 99% identical to SEQ ID NO: 1.

In another embodiment, the anti-CdtB antibody is an antibody that binds specifically to a 17 residue peptide of CdtB (e.g., 17 residues of SEQ. ID NOs: 1 or 5). In one embodiment, the 17 residue peptide has the following sequence: LDYAITGNSNRQQTYTP (SEQ ID NO:3).

In other embodiments, the anti-CdtB antibody is an antibody that binds specifically to a 17 residue peptide that has at least 80%, 85%, 90%, 95%, 96%, 97%, 98%, 99% or 100% homology with 17 contiguous residues of CdtB (e.g., 17 contiguous residues of SEQ. ID NOs: 1 or 5). In one embodiment, the 17 residues of CdtB have the following sequence: LDYAITGNSNRQQTYTP (SEQ ID NO:3).

In other embodiments, the anti-CdtB antibody is an antibody that binds specifically to a polypeptide comprising 17 residues that have at least 80%, 85%, 90%, 95%, 96%, 97%, 98%, 99% or 100% homology with 17 contiguous residues of CdtB (e.g., 17 residues of SEQ. ID NOs: 1 or 5). In one embodiment, the 17 contiguous residues of CdtB have the following sequence: LDYAITGNSNRQQTYTP (SEQ ID NO:3).

In another embodiment, the anti-CdtB antibody is an antibody that antibody binds specifically to an 18 residue peptide having the following sequence: CLDYAITGNSNRQQTYTP (SEQ ID NO:4). The cysteine at the N-terminus was added to SEQ ID NO:3 for purposes of conjugation.

In other embodiments, the anti-CdtB antibody is an antibody that binds specifically to a polypeptide comprising 18 residues that have at least 80%, 85%, 90%, 95%, 96%, 97%, 98%, 99% or 100% homology to CLDYAITGNSNRQQTYTP (SEQ ID NO:4).

In another embodiment, the anti-CdtB antibody is an antibody that binds specifically to a 5, 6, 7, 8, 9, 10, 11, 12, 13, 14, 15, 16, 17, 18, 19, 20, 21, or 22 residue peptide that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB (e.g., 5, 6, 7, 8, 9, 10, 11, 12, 13, 14, 15, 16, 17, 18, 19, 20, 21, or 22 contiguous residues of SEQ ID NOs:1 or 5). In another embodiment, the anti-CdtB antibody is an antibody that binds specifically to a polypeptide comprising 5, 6, 7, 8, 9, 10, 11, 12, 13, 14, 15, 16, 17, 18, 19, 20, 21, or 22 residues that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB (e.g., 5, 6, 7, 8, 9, 10, 11, 12, 13, 14, 15, 16, 17, 18, 19, 20, 21, or 22 contiguous residues of SEQ ID NOs:1 or 5). Contiguous residues of SEQ ID NO:1 include those beginning at any amino acid and ending at any amino acid of SEQ ID NO:1. Contiguous residues of SEQ ID NO:5 include those beginning at any amino acid and ending at any amino acid of SEQ ID NO:5.

In another embodiment, the anti-CdtB antibody is an antibody that antibody binds specifically to a 5, 6, 7, 8, 9, 10, 11, 12, 13, 14, 15, 16, or 17 residue peptide that has at least 80%, 85%, 90%, 95%, 96%, 97%, 98%, 99% or 100% homology with 5, 6, 7, 8, 9, 10, 11, 12, 13, 14, 15, 16, or 17 contiguous residues of LDYAITGNSNRQQTYTP (SEQ ID NO:3) (e.g., 5, 6, 7, 8, 9, 10, 11, 12, 13, 14, 15, 16, or 17 contiguous residues of SEQ ID NO:3). In another embodiment, the purified antibody binds specifically to a polypeptide comprising 5, 6, 7, 8, 9, 10, 11, 12, 13, 14, 15, 16, or 17 residues that has at least 80%, 85%, 90%, 95%, 96%, 97%, 98%, 99% or 100% homology with 5, 6, 7, 8, 9, 10, 11, 12, 13, 14, 15, 16, or 17 contiguous residues of SEQ ID NO:3 (e.g., 5, 6, 7, 8, 9, 10, 11, 12, 13, 14, 15, 16, or 17 contiguous residues of SEQ ID NO:3). Contiguous residues of SEQ ID NO: 3 include those beginning at any amino acid and ending at any amino acid of SEQ ID NO: 3.

In another embodiment, the anti-CdtB antibody is an antibody that binds specifically to a 17 residue peptide encoded by the CdtB gene sequence. In particular embodiments, the anti-CdtB antibody is an antibody that binds specifically to a 17 residue peptide encoded by SEQ ID NO: 2. In various embodiments, the anti-CdtB antibody is an antibody that binds specifically to a 14, 15, 16, 17, 18, 19, 20, 21, or 22 residue peptide encoded by SEQ ID NO: 2. In various embodiments, the purified antibody binds specifically to a 14, 15, 16, 17, 18, 19, 20, 21, or 22 residue peptide that has at least 80%, 85%, 90%, 95%, 96%, 97%, 98%, 99% or 100% homology to 14, 15, 16, 17, 18, 19, 20, 21, or 22 contiguous residues encoded by SEQ ID NO: 2. In various embodiments, the anti-CdtB antibody is an antibody that binds specifically to a polypeptide comprising 14, 15, 16, 17, 18, 19, 20, 21, or 22 residues that have at least 80%, 85%, 90%, 95%, 96%, 97%, 98%, 99% or 100% homology to 14, 15, 16, 17, 18, 19, 20, 21, or 22 contiguous residues encoded by SEQ ID NO: 2.

In another embodiment, the anti-CdtB antibody is an antibody that binds specifically to a peptide encoded by the nucleic acid sequence having the following sequence: CTTGATTATGCAATTACAGGAAATTCAAATAGACAACAAACCTATACTCCA (SEQ ID NO:6), which encodes the 17 amino acid peptide of SEQ ID NO. 3. In another embodiment, the anti-CdtB antibody is an antibody that binds specifically to a polypeptide comprising a peptide encoded by SEQ ID NO:6.

In another embodiment, the anti-CdtB antibody is an antibody that binds specifically to CdtB purified from *E. coli* overexpressing a near full-length CdtB ORF. (See Infection and Immunity, December 2000, p. 6535-6541, Vol. 68, No. 12, herein incorporated by reference in its entirety as though fully set forth.)

In various embodiments, when determining the presence or level of anti-vinculin antibodies, vinculin protein or a fragment thereof as described herein is used as the antigen at about 1.2 µg/ml concentration. In other embodiments, the concentration can be about 0.1, 0.2, 0.3, 0.4, 0.5, 0.6, 0.7, 0.8, 0.9, 1.0, 1.1, 1.3, 1.4, 1.5, 1.6, 1.7, 1.8, 1.9 or 2.0 µg/ml concentration. In various embodiments, an about 1:32 dilution of the biological sample (e.g., plasma) is used in the determination of the presence or level of anti-vinculin antibodies. In other embodiments, an about 1:8, 1:10, 1:12; 1:16, 1:20, 1:24, 1:30, 1:36, 1:48, or 1:64 dilution of the biological sample (e.g., plasma) is used in the determination of the presence or level of anti-vinculin antibodies. In other embodiments, an about 1:8 to 1:64 dilution of the biological sample (e.g., plasma) is used in the determination of the presence or level of anti-vinculin antibodies.

In various embodiments, when determining the presence or level of anti-CdtB antibodies, CdtB protein or a fragment thereof as described herein is used as the antigen at about 1.2 µg/ml concentration. In other embodiments, the concentration can be about 0.1, 0.2, 0.3, 0.4, 0.5, 0.6, 0.7, 0.8, 0.9, 1.0, 1.1, 1.3, 1.4, 1.5, 1.6, 1.7, 1.8, 1.9 or 2.0 µg/ml concentration. In various embodiments, a 1:512 dilution of the biological sample (e.g., plasma) is used in the determination of the presence or level of anti-CdtB antibodies. In other embodiments, an about 1:128, 1:256, 1:768, or 1:1024 dilution of the biological sample (e.g., plasma) is used in the determination of the presence or level of anti-CdtB antibodies. In other embodiments, an about 1:100, 1:150, 1:200, 1:250, 1:300, 1:350, 1:400, 1:500, 1:550; 1:600, 1:650, 1:700, 1:750, 1:800, 1:850, 1:900, 1:950, or 1:1000 dilution of the biological sample (e.g., plasma) is used in the determination of the presence or level of anti-CdtB antibodies. In other embodiments, an about 1:100-1:1000 dilution of the biological sample (e.g., plasma) is used in the determination of the presence or level of anti-CdtB antibodies.

Antigens are immobilized for about 8, 9, 10, 11, 12, 13, 14, 15, 16, 17, 18, 19 or 20 hours (e.g., overnight, >16 hours) at about 4° C. onto high-binding plates (e.g., 96-well plates) in Borate Buffered Saline (BBS) at a pH of 8.2. Wells are alternately coated with antigen or left uncoated in BBS to allow determination of non-specific binding of plasma. Wells are blocked with about 3% bovine serum albumin in 1×PBS for about 1 hour at about room temperature. Coated and uncoated wells are then incubated with a 1:512 dilution of plasma for CdtB and a 1:32 dilution of plasma for vinculin for about 1 hour at room temperature. Antibodies to CdtB and vinculin are used as positive controls. This was followed by about 1 hour incubation with HRP conjugated secondary antibodies. Each step is followed by a series of washes using 0.05% PBS-Tween 20. Finally, a 3,3',5,5'-Tetramethylbenzidine (TMB) substrate solution is used for visualization and immediately read on a plate reader (e.g., BioTek Synergy HT; Winooski, Vt.). The optical densities (OD) are read for about 90 minutes at 370 nm and used to compare levels of anti-CdtB or anti-vinculin. Raw OD values were used for the data analysis.

Types of IBS

In various embodiments, the IBS detected by the methods, assays or systems is constipation predominant IBS (C-IBS), diarrhea predominant IBS (D-IBS), alternating IBS (A-IBS) (more recently re-named as mixed (M-IBS)), or post-infectious irritable bowel syndrome (PI-IBS). In various embodiments, the IBS is D-IBS.

In certain embodiments, the subject desiring diagnosis of IBS in accordance to the methods, assays, and systems of the present invention may have one or more symptoms indicative of IBS. Examples of IBS symptoms include but are not limited to diarrhea, constipation, bloating, and abdominal pain.

Biological Samples

Examples of biological samples include but are not limited to body fluids, whole blood, plasma, stool, intestinal fluids or aspirate, and stomach fluids or aspirate, serum, cerebral spinal fluid (CSF), urine, sweat, saliva, tears, pulmonary secretions, breast aspirate, prostate fluid, seminal fluid, cervical scraping, amniotic fluid, intraocular fluid, mucous, and moisture in breath. In particular embodiments of the method, the biological sample may be whole blood, blood plasma, blood serum, stool, intestinal fluid or aspirate or stomach fluid or aspirate. In various embodiments, the biological sample may be whole blood. In various embodiments, the biological sample may be serum. In various embodiments, the biological sample may be plasma.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1—Materials and Methods

Subject Groups

For the validation of this serum marker, subjects from a 180 center large scale randomized controlled therapeutic trial in diarrhea-predominant IBS (D-IBS) were recruited (TARGET 3). Subjects with D-IBS were selected based on the presence of Rome III criteria. 6 Healthy controls were recruited from Cedars-Sinai Medical Center and the Beth Israel Deaconess Medical Center. All healthy controls were screened for prior history of gastrointestinal disease and for active gastrointestinal symptoms based on history and completion of a bowel symptom questionnaire. Subjects with inflammatory bowel disease (IBD) and celiac disease were recruited based on the presence of intestinal complaints and histologic confirmation of chronic inflammatory changes in the colon or small intestine consistent with Crohn's disease, ulcerative colitis (UC) or celiac disease.

Subjects were excluded from the study if they had a history of diabetes, HIV, unstable thyroid disease, and chronic narcotic use. For IBS subjects and healthy controls, bowel surgery (excluding cholecystectomy or appendectomy) was also an exclusion criteria.

Patient Data

Patient demographics were obtained for all subjects including age and gender. In the case of IBD, the type of disease (UC or Crohn's disease).

Plasma Collection

Plasma was collected from all subjects. This was collected by venipuncture in a lavender top tube, centrifuged at 3500 rpm for 15 minutes and then stored frozen at −80° C. until the time of testing. In the case of the D-IBS subjects from TARGET 3, plasma was collected prior to treatment in the trial.

ELISA Testing

ELISAs were performed using either a complete recombinant *Campylobacter* CdtB protein (Creative Biomart, Shirley, N.Y.) or full length vinculin protein (Novoprotein, Short Hills, N.J.) as antigens at 1.2 µg/ml concentration. Antigens were immobilized overnight at 4° C. onto high-binding 96-well plates (Grenier Bio-One, Monroe, N.C.) in Borate Buffered Saline (BBS) (Medicago, Uppsala, Sweden) at a pH of 8.2. Wells were alternately coated with antigen or left uncoated in BBS to allow determination of non-specific binding of plasma. Wells were blocked with 3% bovine serum albumin in 1×PBS for 1 hour at room temperature. Coated and uncoated wells were then incubated with a 1:512 dilution of plasma for CdtB and a 1:32 dilution of plasma for vinculin for 1 hour at room temperature. Antibodies to CdtB and vinculin were used as positive controls. This was followed by 1 hour incubation with HRP conjugated secondary antibodies (Jackson ImmunoResearch, West Grove, Pa.). Each step was followed by a series of washes using 0.05% PBS-Tween 20. Finally, a 3,3',5,5'-Tetramethylbenzidine (TMB) substrate solution (Pierce, Rockford, Ill.) was used for visualization and immediately read on a BioTek Synergy HT plate reader (Winooski, Vt.). The optical densities (OD) were read for 90 minutes at 370 nm and used to compare levels of anti-CdtB or anti-vinculin. Raw OD values were used for the data analysis.

Statistical Analysis (Data w/o Celiac Patients)

Data were expressed as mean±standard error (SE) and exact 95% confidence intervals (CI). Multiple group comparisons were performed using one-way analysis of variance (ANOVA) after equality of variances was confirmed by Bartlett's test. Normality of the data distribution was assessed using histograms with overlapping Kernel density and normal distributions curves. Distribution of anti-vinculin and anti-CdtB normalized after values were transformed to square roots and squares respectively. Student's t-test was used for comparisons of normally distributed variables between two groups. Pearson's chi-squared test was used for comparison of categorical data. Receiver operating characteristic (ROC) curves were constructed using nonparametric methodology. Confidence intervals for areas under curves (AUC) were computed using DeLong's method. Sensitivity, specificity and likelihood ratios of each independent value of anti-vinculin and anti-CdtB to a precision of 0.01 OD were calculated and were assessed to capture the optimal cut-offs. A P value of <0.05 was considered significant. Analysis was performed using STATA version 11.2 (STATA Corp., Texas, USA)

Statistical Analysis (Data w/Celiac Patients)

Numerical variables were summarized by mean±standard deviation. Normality of the data distributions was assessed using histograms with overlapping Kernel density and normal distributions curves. The anti-vinculin distribution was normalized by a square root transformation. Homogeneity of variance was assessed by Bartlett's test.

Student's t-test was used for comparisons of normally distributed variables between two groups. Normally distributed variables were compared across more than two groups by one-way ANOVA and Dunnett's post hoc tests with IBS as the reference group. Categorical variables were summarized by frequency and percent. Pearson's chi-square test was used for comparison of categorical data. Receiver operating characteristic (ROC) curves were constructed in the standard fashion. Confidence intervals for areas under curves (AUC) were computed using the method of DeLong et al 21. Sensitivity, specificity and likelihood ratios of anti-vinculin and anti-CdtB to a precision of 0.01 OD were calculated and were assessed to obtain the favorable cut-offs. The 0.05 significance level was used throughout. Statistical analysis was performed using STATA version 11.2 (STATA Corp., Texas, USA) and SAS version 9.3 (SAS Institute, Cary, N.C., USA).

Example 1—Results

Patient Demographics (w/o Analysis Relating to Celiac Patients)

In total, 2767 subjects were recruited (Table 1A). This included 2564 D-IBS subjects, 43 healthy subjects, 10 celiac and 150 IBD subjects (n=78 Crohn's, 72 ulcerative colitis (UC)). There were significantly more females in the healthy volunteers, IBS and celiac cohorts as compared with the IBD cohort (P=0.01). IBS subjects were on average 6.7 years older than non-MS subjects (P<0.01). Age was not significantly different between the other groups.

TABLE 1A

Patient demographics.

| | Number of subjects | Age | % of females |
|---|---|---|---|
| Healthy controls | 43 | 36.0 ± 9.9 | 67.4 |
| IBS | 2564 | 46.4 ± 13.6 | 68.2 |
| CD | 78 | 41.8 ± 13.1 | 56.4 |
| UC | 72 | 40.2 ± 12.9 | 55.5 |
| IBD (UC + CD) | 150 | 41.0 ± 13.0 | 56.0 |
| Celiac disease | 10 | 35.6 ± 10.3 | 70 |

Values are given as mean ± SD;
OD—optical density;
CD—Crohn's disease,
UC—ulcerative colitis Patient Demographics (w/Analysis Relating to Celiac Patients)

In total, 2681 subjects were recruited (Table 1B). This included 2375 D-IBS subjects, 43 healthy subjects, 121 celiac and 142 IBD subjects (n=73 Crohn's, n=69 ulcerative colitis). IBS subjects were on average 3.9 years older than the non-IBS groups (p<0.001). There were no differences in sex distribution of IBS and non-IBS subjects; however, percentage of females was greater in the healthy controls, IBS and celiac groups as compared with the IBD group (P<0.001).

TABLE 1B

Patient demographics.

| | Number of subjects | Age (range) | % of females |
|---|---|---|---|
| Healthy controls | 43 | 36.0 ± 9.9 (22-62) | 67.4 |
| D-IBS | 2375 | 44.4 ± 12.2 (18-65) | 67.6 |
| CD | 73 | 40.6 ± 11.3 (18-65) | 56.2 |
| UC | 69 | 41.2 ± 12.2 (19-63) | 55.1 |
| IBD (UC + CD) | 142 | 40.9 ± 11.7 (18-65) | 55.6 |
| Celiac disease | 121 | 41.6 ± 12.3 (19-65) | 76 |

Values are given as mean ± standard deviation,
CD—Crohn's disease,
UC—ulcerative colitis.

ELISA Comparisons Between Groups (w/o Celiac Patients)

Anti-CdtB levels in IBS subjects were significantly higher than in all non-IBS subjects (2.54±0.01 (95% CI 2.52-2.57)

compared to 1.68±0.05 (95% CI 1.58-1.79)) (P<0.001) (FIG. 1A). There were no significant differences in anti-CdtB levels among non-IBS subjects (F-test P=0.25).

Figure 2A:
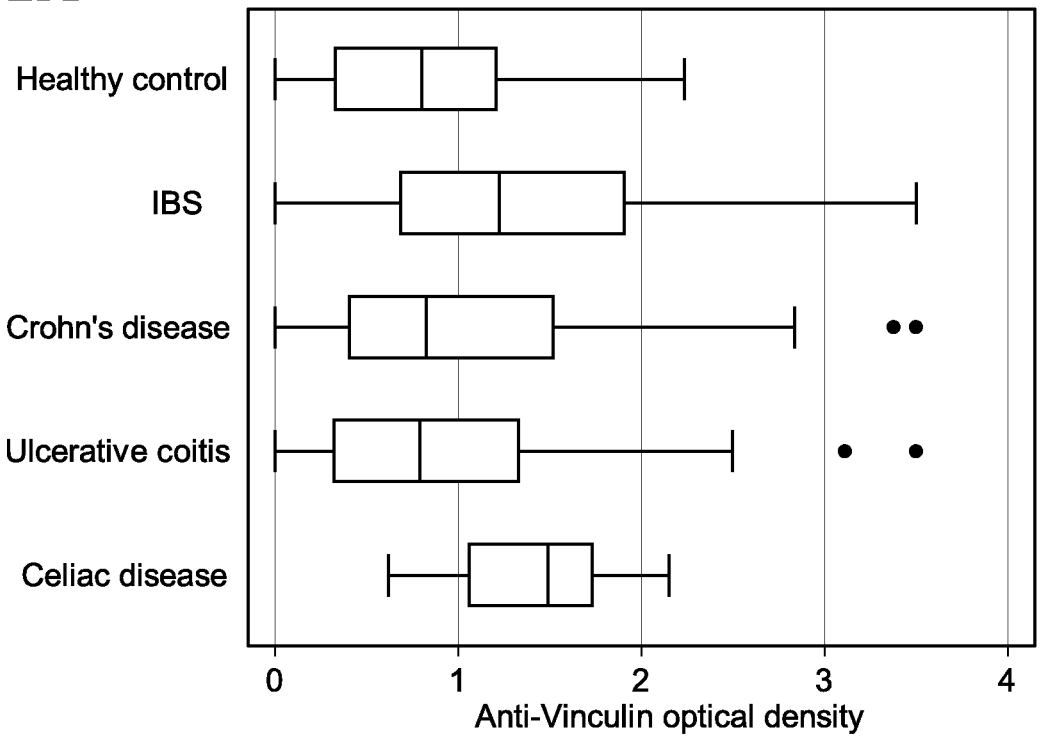
FIG. 2A depicts comparison of anti-vinculin antibody OD among the groups in accordance with various embodiments of the present invention.
Figure 2B:
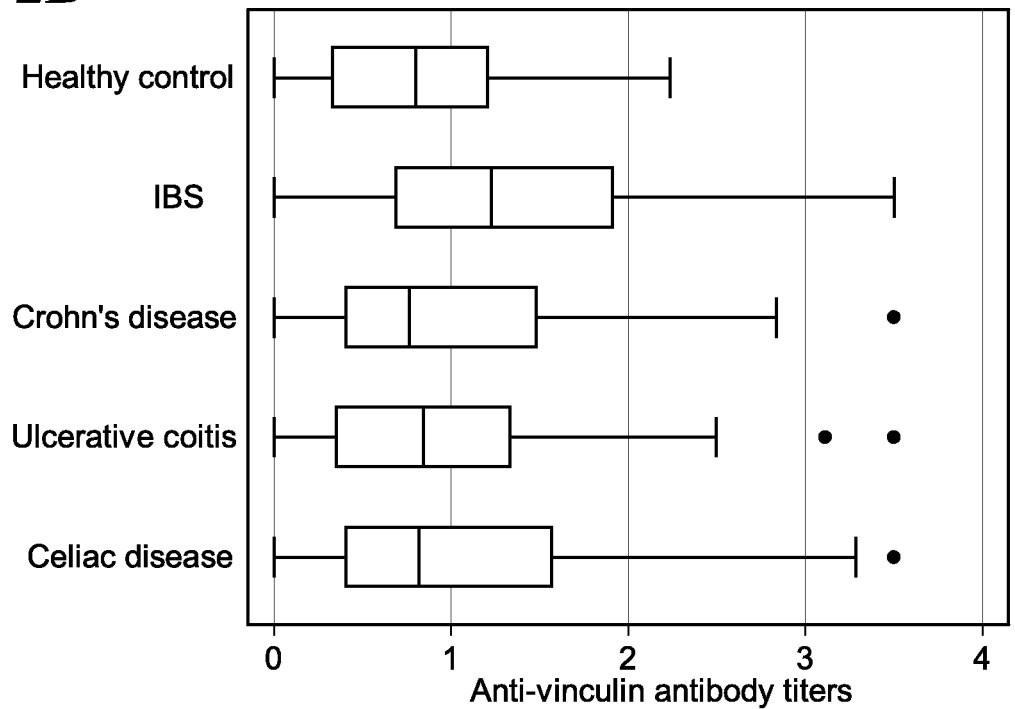
FIG. 2B depicts comparison of optical density (OD) for the anti-vinculin antibody among the groups. Dots represent outlier subjects beyond the whisker plot. Titers were higher in IBS subjects as compared to any other group (p<0.001)

Anti-vinculin levels were significantly higher in IBS subjects when compared to all non-IBS subjects (1.3334±0.02 (95% CI 1.30-1.37) compared to 1.01±0.06 (95% CI 0.89-1.12)) (P<0.001) (FIG. 2A). Differences in anti-vinculin levels among non-IBS subjects were not statistically significant (F-test P=0.08).

ELISA Comparisons Between Groups (w/Celiac Patients)

Figure 1B:
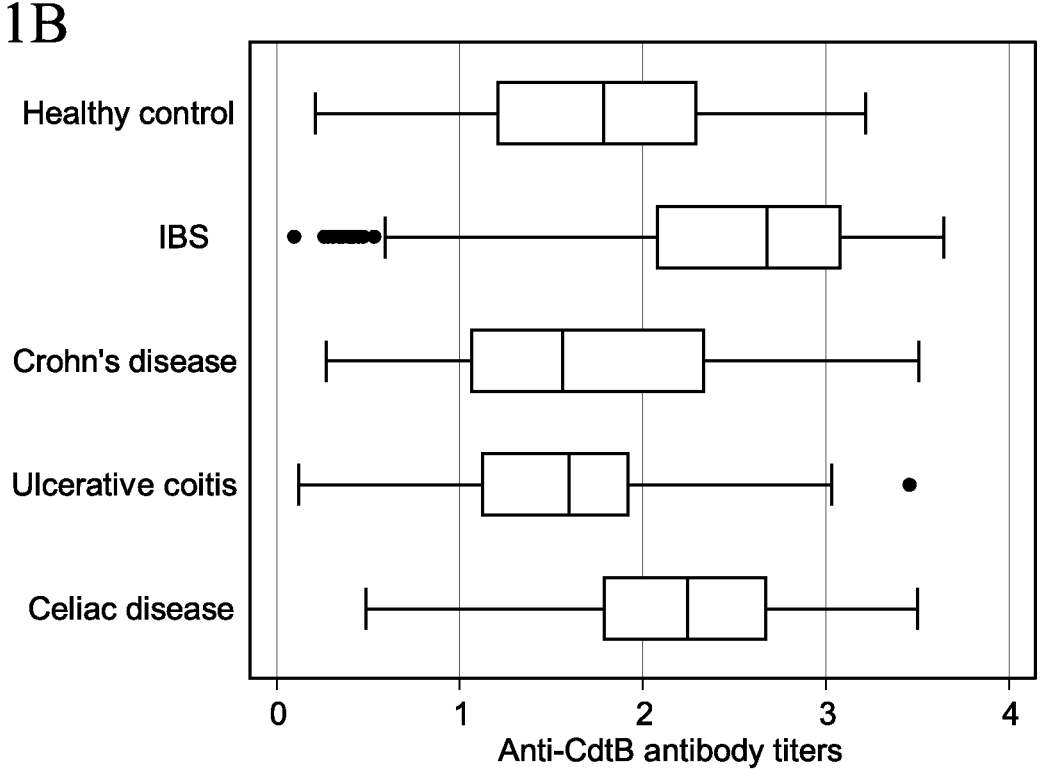
FIG. 1B depicts comparison of optical density (OD) for the anti-CdtB antibody among the groups. Dots represent outlier subjects beyond the whisker plot. Titers were higher in IBS subjects in comparison to any other group (p<0.001) Titers were higher in subjects with celiac disease as compared to healthy controls and IBD subjects (p<0.001)

Using optical density levels, anti-CdtB antibody levels in D-IBS subjects (2.53±0.69) were significantly higher than healthy subjects (1.81±0.73), Crohn's disease (1.72±0.81), ulcerative colitis (1.54±0.68) and celiac disease (2.23±0.70) (P<0.001) (FIG. 1B). There were no differences in anti-CdtB levels between healthy subjects and IBD subjects (p=0.23); however, subjects with celiac disease had higher anti-CdtB levels than all other non-IBS groups (p<0.001).

Anti-vinculin levels were also significantly higher in D-IBS subjects (1.34±0.85) when compared to healthy subjects (0.81±0.59), Crohn's disease (1.05±0.91), ulcerative colitis (0.96±0.77) and celiac disease (1.07±0.98) (P<0.0001) (FIG. 1B). Differences in anti-vinculin levels among non-IBS subjects were not statistically significant.

Sensitivity and Specificity Analyses (w/o Celiac Patients)

Figure 3A:
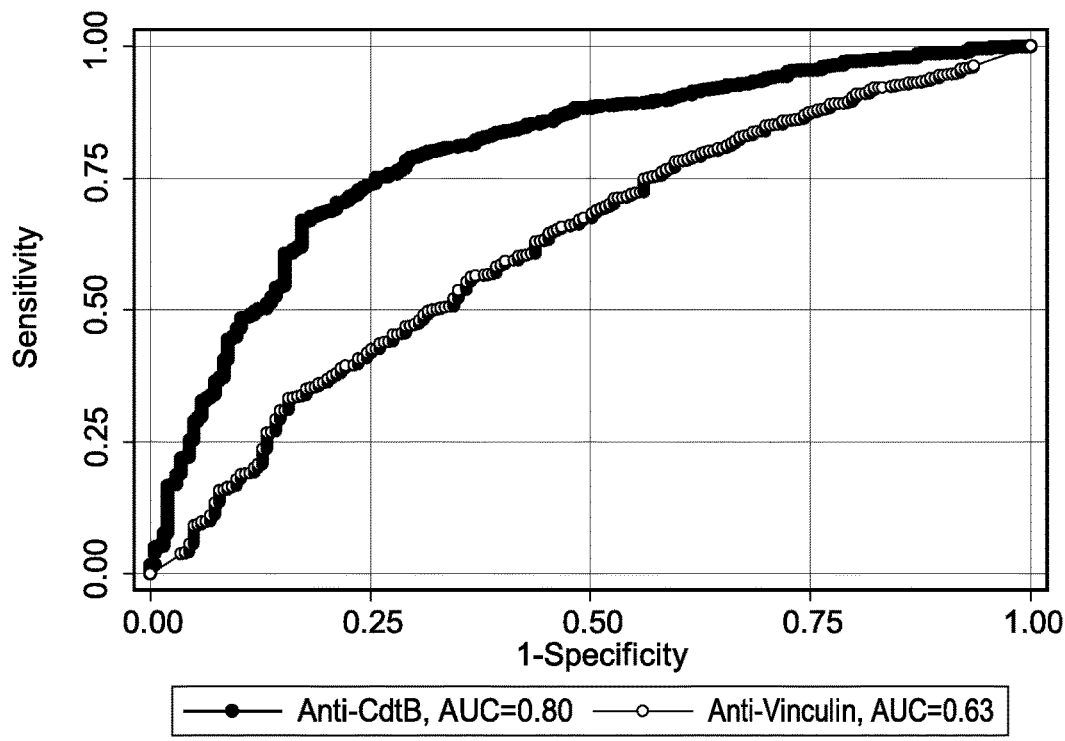
FIG. 3A depicts receiver operator curve (ROC) comparing anti-CdtB and anti-vinculin levels between IBS subjects and all non-IBS subjects in the study in accordance with various embodiments of the present invention. (Anti-CdtB—top line; anti-vinculin—bottom line.)
Figure 4:
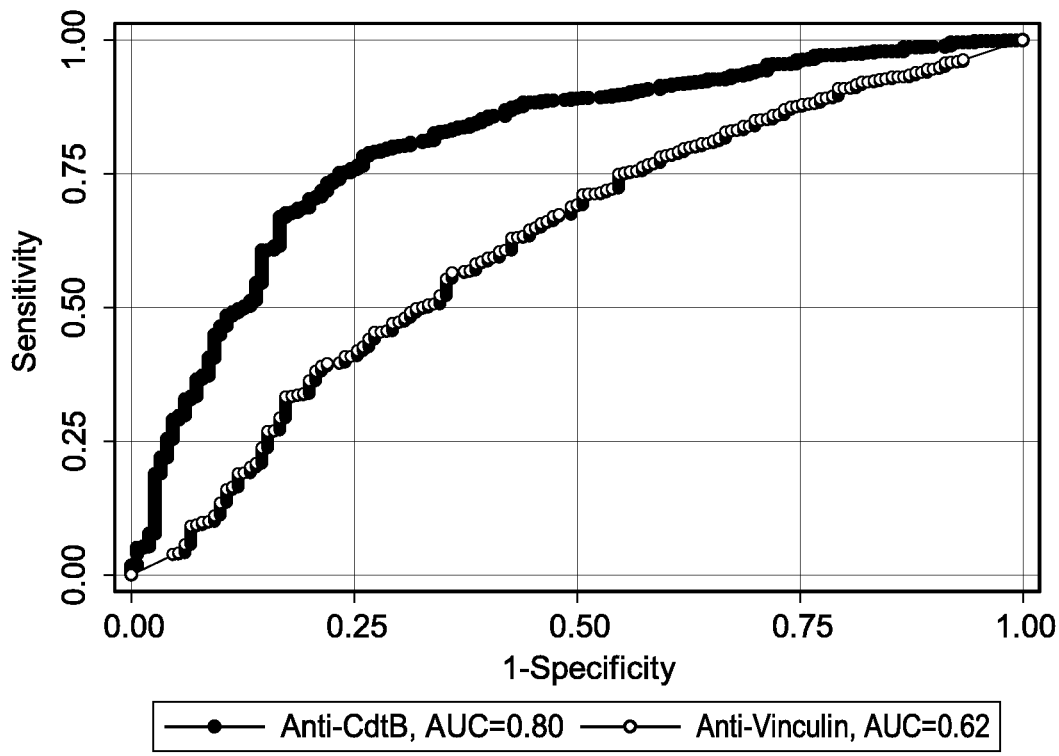
FIG. 4 depicts receiver operator curve (ROC) comparing anti-CdtB and anti-vinculin levels between IBS subjects and all IBD subjects in the study in accordance with various embodiments of the present invention. (Anti-CdtB—top line; anti-vinculin—bottom line.)
Figure 5:
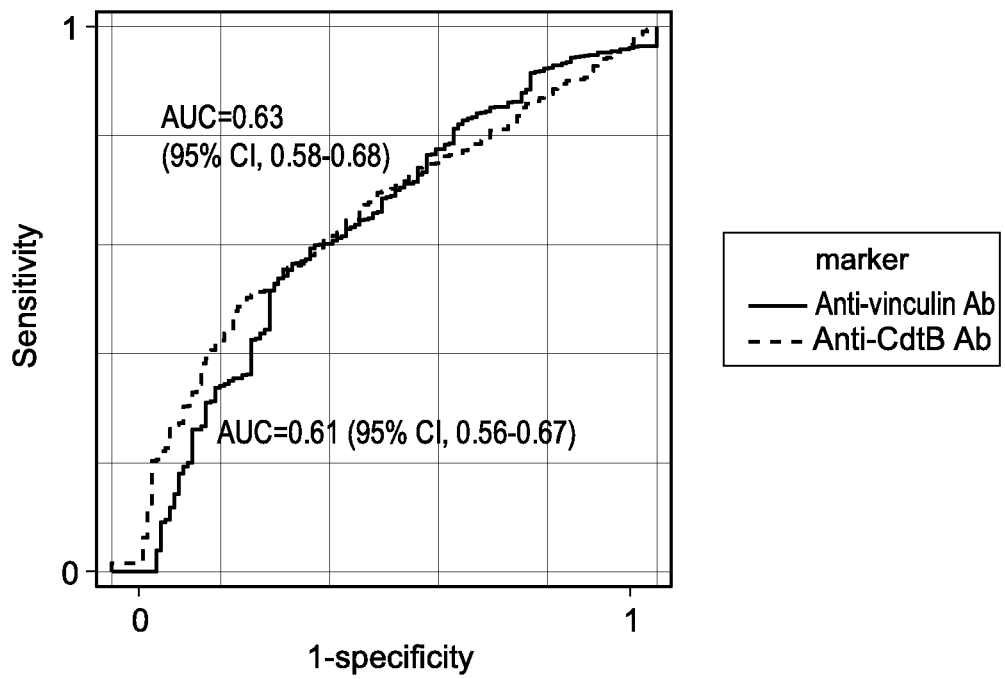
FIG. 5 depicts receiver operator curve (ROC) comparing anti-CdtB and anti-vinculin levels between IBS and celiac subjects. (Anti-CdtB—top line at the beginning; anti-vinculin—bottom line at the beginning.)
Figure 6:
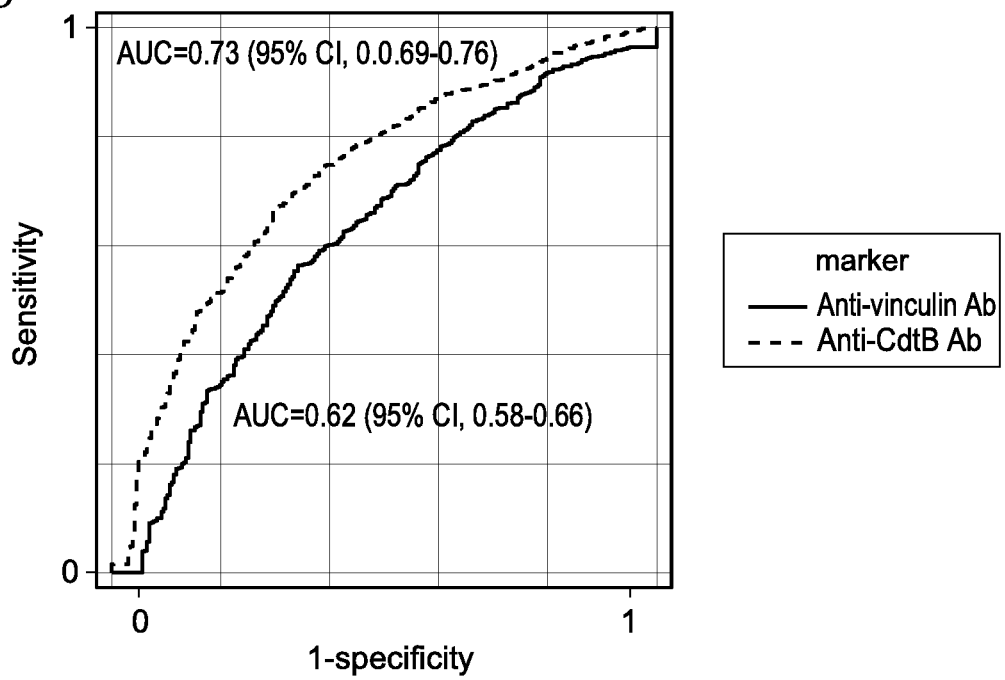
FIG. 6 depicts receiver operator curve (ROC) comparing anti-CdtB and anti-vinculin levels between IBS and non-IBS subjects with chronic diarrhea (i.e., CD, UC and celiac disease). (Anti-CdtB—top line; anti-vinculin—bottom line.)
Figure 7:
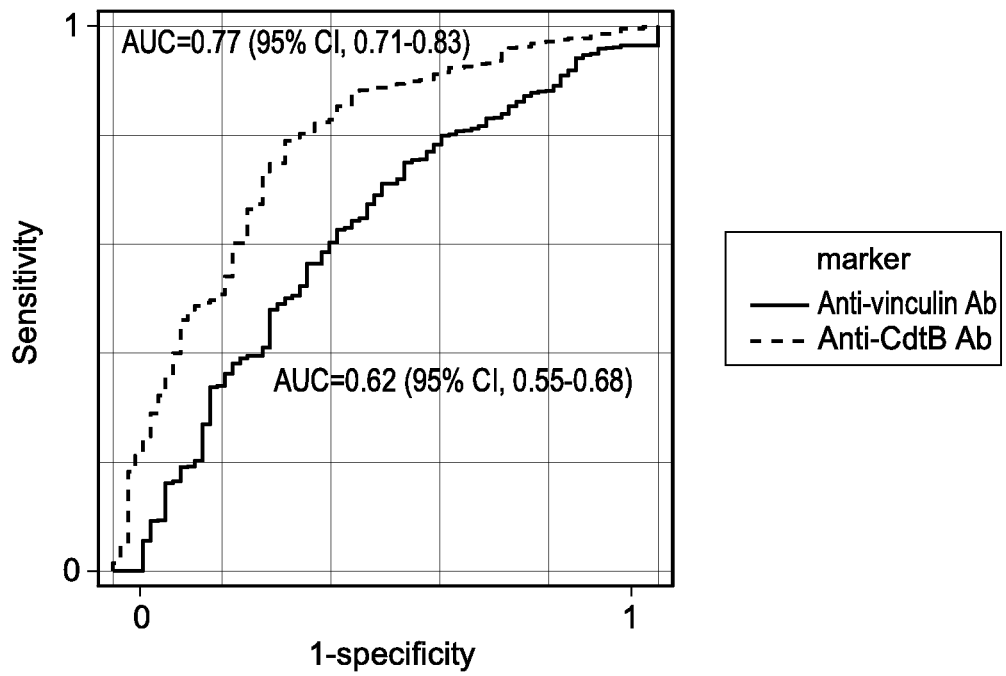
FIG. 7 depicts receiver operator curve (ROC) comparing anti-CdtB and anti-vinculin levels between IBS and CD subjects. (Anti-CdtB—top line; anti-vinculin—bottom line.)
Figure 8:
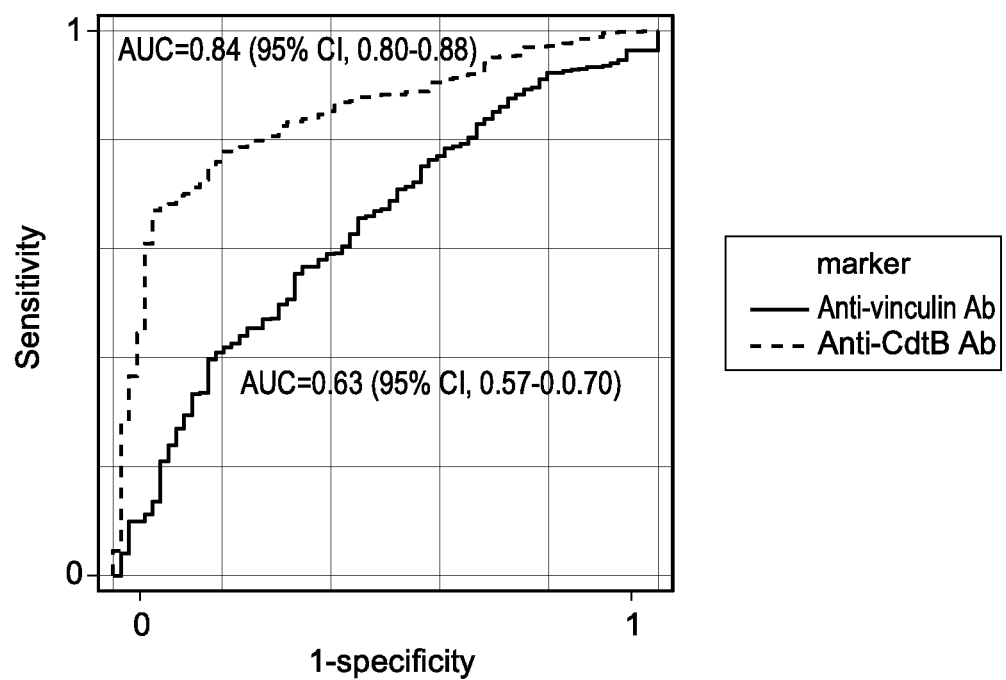
FIG. 8 depicts receiver operator curve (ROC) comparing anti-CdtB and anti-vinculin levels between IBS and UC subjects. (Anti-CdtB—top line; anti-vinculin—bottom line.)

Receiver operating characteristics (ROC) were used to assess the utility of anti-vinculin and anti-CdtB levels in differentiating IBS subjects from non-IBS, IBD and healthy individuals. FIGS. 3A and 4 demonstrate the ROC curves for these two tests when comparing IBS subjects to all non-IBS subjects and to IBD subjects, respectively. The anti-CdtB test performed better than anti-vinculin and appeared equally discriminating of IBS from all non-IBS subjects and from the IBD group alone. In subgroup analysis, there appeared to be no difference based on the type of IBD (data not shown). The ROC curve for both anti-CdtB and anti-vinculin show that D-IBS can be discriminated from healthy subjects based on this test.

The optical density (OD) levels for each test were then used to determine the ideal threshold for identification of D-IBS. Tables 2A and 3A demonstrate some potential optical density thresholds for the identification of IBS based on sensitivity, specificity and likelihood ratio. For D-IBS, a higher specificity even when associated with a lower sensitivity is more desirable. In D-IBS an ideal test would definitively diagnose IBS, thus reducing the need for invasive testing. So specificity and likelihood ratio was deemed more important. Based on the ROC curves, the ideal level for anti-CdtB appeared to be a level of ≥2.48 and for anti-vinculin the optimal level was of ≥1.62 appear to optimize specificity with relatively limited effects on sensitivity.

TABLE 2A

Favorable cutoffs of anti-CdtB for diagnosis of IBS over other causes

| OD | Specificity % | Sensitivity % | +LR | −LR |
|---|---|---|---|---|
| ≥2.48 | 84.7 | 60.7 | 4.0 | 0.5 |
| ≥2.79 | 91.1 | 44.4 | 5.0 | 0.6 |

OD—optical density,
+LR - positive likelihood ratio,
−LR - negative likelihood ratio

TABLE 3A

Favorable cutoffs of anti-vinculin for diagnosis of IBS over other causes

| OD | Specificity % | Sensitivity % | +LR | −LR |
|---|---|---|---|---|
| ≥1.62 | 82.3 | 35.0 | 2.0 | 0.78 |
| ≥1.86 | 86.7 | 26.5 | 2.0 | 0.8 |
| ≥2.23 | 92.1 | 15.7 | 2.0 | 0.9 |

OD—optical density,
+LR—positive likelihood ratio,
−LR—negative likelihood ratio Sensitivity and Specificity Analyses (w/Celiac Patients)

Figure 3B:
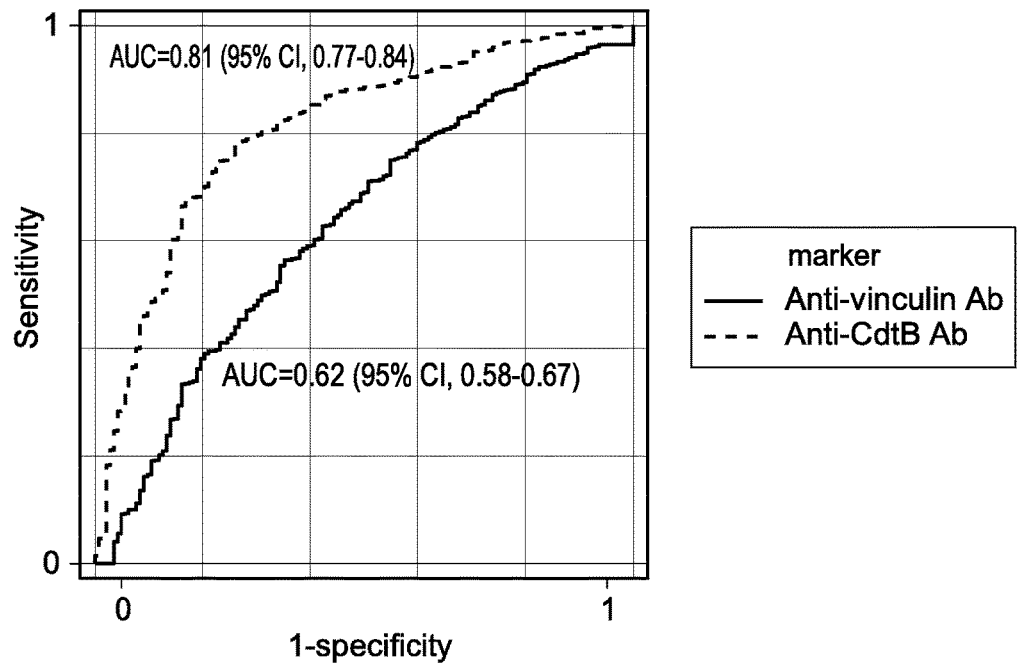
FIG. 3B depicts receiver operator curve (ROC) comparing anti-CdtB and anti-vinculin levels between IBS subjects and IBD subjects in the study. AUC, Area under the curve; CI, confidence interval. (Anti-CdtB—top line; anti-vinculin—bottom line.)
Figure 3C:
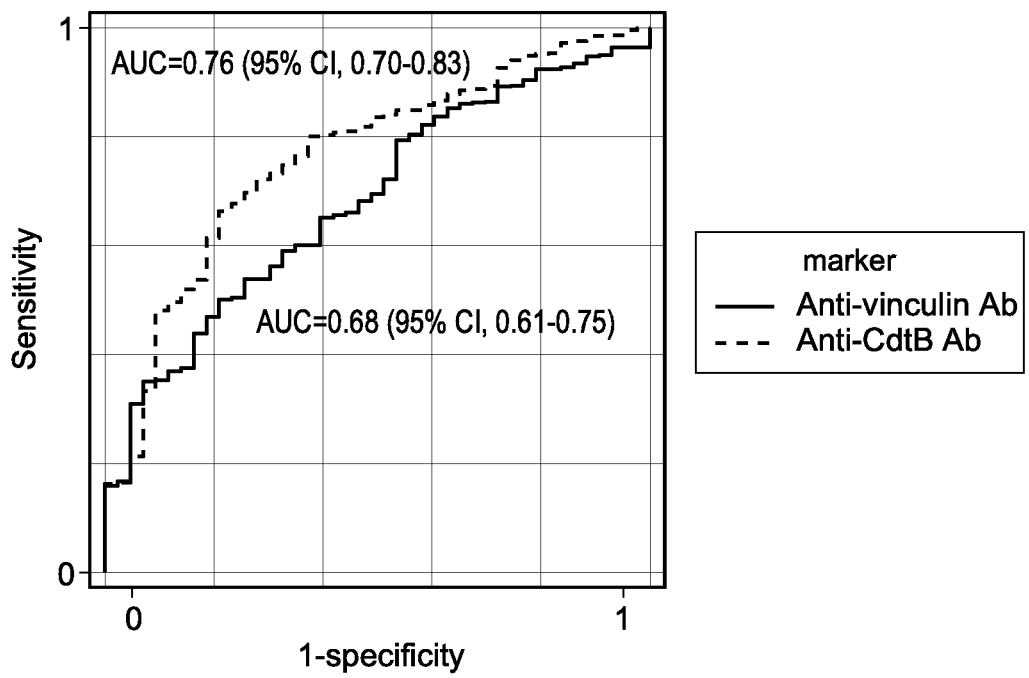
FIG. 3C depicts receiver operator curve (ROC) comparing anti-CdtB and anti-vinculin levels between IBS subjects and healthy subjects in the study. (Anti-CdtB—top line; anti-vinculin—bottom line.)

Receiver operating characteristics (ROC) were used to assess the utility of anti-vinculin and anti-CdtB levels in differentiating D-IBS subjects from IBD subjects. FIG. 3B demonstrates the ROC curves for these two tests when comparing D-IBS subjects to IBD subjects. While both tests were effective at discriminating D-IBS subjects from the IBD group, the area-under-the-curve (AUC) for the diagnosis of D-IBS vs. IBD was higher for anti-CdtB than for anti-vinculin (0.81 and 0.62, respectively). In subgroup analysis, there appeared to be no difference based on the type of IBD (data not shown). The ROC curves for D-IBS compared to non-IBS, celiac subjects and healthy controls were also discriminatory.

The optical density (OD) levels for each test were then used to determine the ideal threshold for identification of D-IBS as compared to IBD. Tables 2B and 3B demonstrate some potential optical density thresholds for the identification of D-IBS based on sensitivity, specificity and likelihood ratio. An ideal test would definitively diagnose IBS, thus reducing the need for invasive testing. Therefore, we focused on specificity and positive likelihood ratio. Based on this, the ideal threshold for anti-CdtB to identify D-IBS appeared to be >2.80, while for anti-vinculin the optimal threshold appeared to be >1.68.

TABLE 2B

Favorable cut offs for anti-CdtB for the diagnosis of D-IBS over IBD

| OD | Specificity % | Sensitivity % | +LR | −LR |
|---|---|---|---|---|
| ≥2.49 | 85.9 | 60.0 | 4.3 | 0.5 |
| ≥2.80 | 91.6 | 43.7 | 5.2 | 0.6 |
| ≥3.04 | 95.8 | 28.3 | 6.7 | 0.7 |

OD—optical density,
+LR—positive likelihood ratio,
−LR—negative likelihood ratio

TABLE 3B

Favorable cut offs for anti-vinculin for the diagnosis of D-IBS over IBD

| OD | Specificity % | Sensitivity % | +LR | −LR |
|---|---|---|---|---|
| ≥1.53 | 80.3 | 37.8 | 1.9 | 0.8 |
| ≥1.68 | 83.8 | 32.6 | 2.0 | 0.8 |
| ≥1.80 | 84.5 | 28.9 | 1.8 | 0.8 |

OD—optical density,
+LR—positive likelihood ratio,
−LR—negative likelihood ratio Gender Effect on Biomarker (w/o Celiac Patients)

Anti-CdtB and anti-vinculin levels were also compared in females only and in males only. Despite gender differences between subjects with D-IBS and control groups, both biomarkers could be used to successfully identify D-IBS in both males and females.

Headings used herein are simply for organization and are not intended to limit the disclosure in any manner. The content of any individual section may be equally applicable to all sections.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. An assay system for distinguishing irritable bowel syndrome (IBS) from inflammatory bowel disease (IBD) and celiac disease, comprising:
   a biological sample obtained from a subject desiring a diagnosis to distinguish IBS from both IBD and celiac disease,
   vinculin or a fragment thereof and cytolethal distending toxin subunit B (CdtB) or a fragment thereof; and
   one or more assays to detect in the biological sample, levels of anti-vinculin antibodies and anti-cytolethal distending toxin subunit B (CdtB) antibodies.

2. The system of claim 1, wherein the biological sample is whole blood, serum, or plasma.

3. The system of claim 1, wherein the biological sample is plasma.

4. The system of claim 1, wherein the one or more assays comprises an assay to detect levels of anti-vinculin antibodies and an assay to detect levels of anti-CdtB antibodies.

5. The system of claim 4, wherein the assay to detect levels of anti-vinculin antibodies comprises vinculin or a fragment thereof.

6. The system of claim 4, wherein the assay to detect levels of anti-CdtB antibodies comprises CdtB or a fragment thereof.

7. The system of claim 4, wherein the assay to detect levels of anti-vinculin antibodies and the assay to detect levels of anti-CdtB antibodies are enzyme-linked immunosorbent assays (ELISAs).

* * * * *